United States Patent
MacKenzie et al.

[11] Patent Number: 6,071,938
[45] Date of Patent: Jun. 6, 2000

[54] BENZOPYRANS

[75] Inventors: Alexander Roderick MacKenzie; Sandra Marina Monaghan, both of Sandwich, United Kingdom

[73] Assignee: Pfizer Inc., New York, N.Y.

[21] Appl. No.: 09/288,975

[22] Filed: Apr. 9, 1999

Related U.S. Application Data

[62] Division of application No. 08/591,500, filed as application No. PCT/EP94/02387, Jul. 18, 1994, Pat. No. 5,912,244.

[30] Foreign Application Priority Data

Aug. 4, 1993 [GB] United Kingdom ............... 9316111

[51] Int. Cl.[7] .......................... A61K 31/35; A61K 31/44; C07D 303/17; C07D 311/94; C07D 405/06
[52] U.S. Cl. .......................... 514/337; 514/456; 514/460; 546/283.1; 549/399; 549/400; 549/401; 549/403; 549/404; 549/545
[58] Field of Search ................... 514/456, 460, 514/337; 549/399, 400, 401, 403, 404, 545; 546/283.1

[56] References Cited

U.S. PATENT DOCUMENTS

| | | | |
|---|---|---|---|
| 4,999,371 | 3/1991 | Englert et al. | 514/422 |
| 5,112,972 | 5/1992 | Gericke et al. | 544/230 |

FOREIGN PATENT DOCUMENTS

| | | |
|---|---|---|
| 0277611 | 8/1988 | European Pat. Off. |
| 0277612 | 8/1989 | European Pat. Off. |
| 0337179 | 10/1989 | European Pat. Off. |
| 0340718 | 11/1989 | European Pat. Off. |
| 0346724 | 12/1989 | European Pat. Off. |
| 0351720 | 1/1990 | European Pat. Off. |
| 0355565 | 2/1990 | European Pat. Off. |
| 0363883 | 4/1990 | European Pat. Off. |
| 0400430 | 12/1990 | European Pat. Off. |
| 0450415 | 10/1991 | European Pat. Off. |
| 0547523 | 6/1993 | European Pat. Off. |
| 0552679 | 7/1993 | European Pat. Off. |
| 0331189 | of 1989 | Ireland. |
| 2242628 | 10/1991 | United Kingdom. |

*Primary Examiner*—Johann Richter
*Assistant Examiner*—Jane C. Oswecki
*Attorney, Agent, or Firm*—Peter C. Richardson; Gregg C. Benson; James T. Jones

[57] ABSTRACT

A compound of the formula:

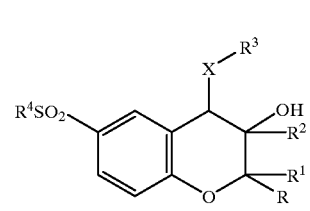

(I)

or a pharmaceutically acceptable salt thereof, wherein X, O R, $R^1$, $R^2$, $R^3$, and $R^4$ are defined in the specification; compositions containing such compounds; intermediates used in the preparation of such compounds; and methods for treating a disease associated with the altered tone and/or motility of smooth muscle, for example chronic obstructive airways disease, asthma, urinary incontinence, irritable bowel syndrome, diverticular disease, oesophageal achalasia, and hypertension.

11 Claims, No Drawings

BENZOPYRANS

This is a divisional of application Ser. No. 08/591,500, filed Jul. 8, 1996, now U.S. Pat. No. 5,912,244 which is a National Stage Filing under 35 U.S.C. §371 based on PCT/EP94/02387 which was filed internationally on Jul. 18, 1994.

The present invention relates to benzopyrans. More particularly it relates to 6-(hydroxyphenyl)sulphonylbenzo[b] pyran derivatives and to compositions containing, uses of, processes for the preparation of and intermediates used in the preparation of, such derivatives.

The present derivatives display smooth muscle relaxant activity by a mechanism involving potassium channel opening. They are therefore useful in the curative or prophylactic treatment of diseases associated with the altered tone and/or motility of smooth muscle which can, for example, occur in the lung, bladder, gut, uterus or cardiovascular system. Such diseases include chronic obstructive airways disease, asthma, urinary incontinence, irritable bowel syndrome, diverticular disease, oesophageal achalasia and hypertension. In addition, the present derivatives may be useful in the treatment of peripheral vascular disease, congestive heart failure, pulmonary hypertension, myocardial and cerebral ischaemia, angina, male pattern baldness, cardiac arrhythmia, skeletal muscle fatigue/paralysis (myotonic muscular dystrophy), glaucoma, epilepsy, tinnitus, vertigo and dysmenorrhoea.

EP-A-0547523, EP-A-0351720, EP-A-0450415 and EP-A-0400430 disclose benzopyrans with pharmacological activity. EP-A-0552679 describes epoxidation of chromenes.

The present invention provides compounds of the formula:

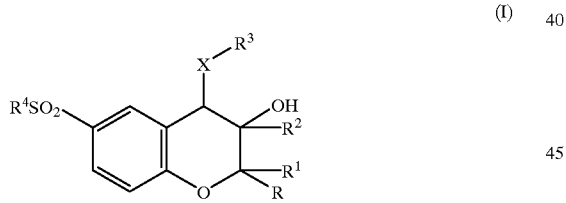

(I)

and the pharmaceutically acceptable salts thereof, wherein X is O, S or NH;

R and $R^1$ are each independently selected from H and $C_1$–$C_4$ alkyl or taken together represent $C_2$–$C_6$ alkylene;

$R^2$ is H or $C_1$–$C_4$ alkyl;

$R^3$ is (a) a 6-membered heterocyclic ring containing 1 or 2 N hetero-atoms, said ring being linked to X by a ring carbon atom, optionally benzo-fused and optionally substituted, including in the benzo-fused portion, by $C_1$–$C_6$ alkyl, hydroxy, —$OR^5$, halo, —$S(O)_mR^5$, oxo, amino, —$NHR^5$, —$N(R^5)_2$, cyano, —$CO_2R^5$, —$CONH_2$, —$CONHR^5$, or —$CON(R^5)_2$, with the proviso that $R^3$ is not an N—($C_1$–$C_6$ alkyl)pyridonyl group;

(b), when X is NH, a group of the formula:

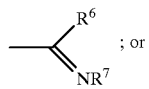

; or (c), when X is NH, a group of the formula:

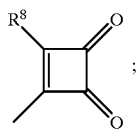

;

$R^4$ is phenyl substituted by a hydroxy group and optionally further substituted by 1 or 2 substituents each independently selected from hydroxy, $C_1$–$C_6$ alkyl, —$OR^5$, halo, cyano and nitro;

$R^5$ is $C_1$–$C_6$ alkyl;

$R^6$ is —$OR^5$, —$NHR^5$, —$N(R^5)_2$, —$SR^5$ or —$NHR^9$;

$R^7$ is cyano;

$R^8$ is —$OR^5$, —$NHR^5$, —$N(R^5)_2$ or —$NHR^9$;

$R^9$ is phenyl optionally substituted by $C_1$–$C_6$ alkyl, hydroxy, —$OR^5$, halo, cyano or nitro; and m is 0, 1 or 2.

In the above definitions, the term "halo" means fluoro, chloro, bromo or iodo. Alkyl groups containing three or more carbon atoms may be straight- or branched-chain.

Preferably X is O or NH.

Most preferably X is O.

Preferably R, $R^1$ and $R^2$ are each $C_1$–$C_4$ alkyl.

Most preferably R, $R^1$ and $R^2$ are each methyl.

Preferably $R^3$ is (a) a 6-membered heterocyclic ring containing 1 or 2 N hetero-atoms, said ring being optionally benzo-fused and optionally substituted by $C_1$–$C_4$ alkyl, hydroxy, halo or oxo, and more preferably said ring is not fully saturated, (b) is a group of the formula:

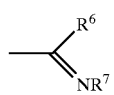

or (c) is a group of the formula:

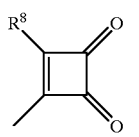

More preferably $R^3$ is 1,2-dihydro-2-oxo-1H-pyridin-4-yl, 1,2-dihydro-5,6-dimethyl-2-oxo-1H-pyridin-4-yl, 3-hydroxypyridazin-6-yl, 2,3-dihydro-2-methyl-3-oxopyridazin-6-yl, 2,3-dihydro-2-ethyl-3-oxopyridazin-6-yl, 1,2-dihydro-1-oxo-2H-phthalazin-4-yl, 1,2-dihydro-2-methyl-1-oxophthalazin-4-yl, 2-chloropyrimidin-4-yl, 3,4-dioxo-2-ethoxycyclobut-1-en-1-yl or 3-cyano-2-methylisothioureido.

Most preferably $R^3$ is 1,2-dihydro-2-oxo-1H-pyridin-4-yl or 2,3-dihydro-2-methyl-3-oxopyridazin-6-yl.

Preferably $R^4$ is phenyl substituted by one or two hydroxy group(s). More preferably $R^4$ is 2-, 3- or 4-hydroxyphenyl, or is 3,4-dihydroxyphenyl. Most preferably $R^4$ is 3-hydroxyphenyl or 4-hydroxyphenyl.

Preferably $R^6$ is —$SR^5$.

Most preferably $R^6$ is methylthio.

Preferably $R^8$ is —$OR^5$.

Most preferably $R^8$ is ethoxy.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate, and p-toluenesulphonate salts.

Suitable base salts are formed from bases which form non-toxic salts and examples are the aluminium, calcium, magnesium, zinc and diethanolamine salts.

For a review on suitable salts see Berge et al, J. Pharm. Sci., 1977, 66, 1–19.

A compound of the formula (I) may contain one or more asymmetric carbon atoms and may therefore exist in two or more stereoisomeric forms. The present invention includes the individual stereoisomers of the compounds of the formula (I) and mixtures thereof, together, where appropriate, with all the tautomeric forms of the compounds of the formula (I).

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

A preferred group of compounds of the formula (I) has the formula:

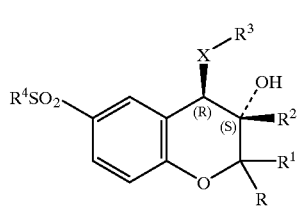

(IA)

where X, R, $R^1$, $R^2$, $R^3$ and $R^4$ are as previously defined for a compound of the formula (I).

The compounds of the formula (I) provided by the invention can be prepared by the following methods:

1) All the compounds of the formula (I) can be prepared by deprotection of a compound of the formula:

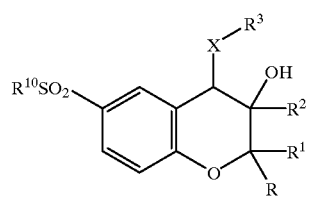

(II)

where $R^{10}$ is phenyl substituted by a protected hydroxy group and optionally further substituted by 1 or 2 substituents each independently selected from a protected hydroxy group, hydroxy, $C_1$–$C_6$ alkyl, —$OR^5$, halo, cyano and nitro, and X, R, $R^1$, $R^2$, $R^3$ and $R^5$ are as previously defined for a compound of the formula (I).

A variety of suitable hydroxy protecting groups together with methods for their removal are well known in the art to the skilled person, e.g. see T. W. Greene and P. G. M. Wuts, "Protective Groups in Organic Synthesis", Second Edition, Wiley-lnterscience, 1991.

Certain alkyl groups, e.g. methyl and t-butyl, can be regarded as hydroxy protecting groups. It should therefore be realised that when the $R^{10}$ phenyl group is substituted by $C_1$–$C_4$ alkoxy, e.g. methoxy or t-butoxy, it may also be converted to a hydroxyphenyl group using certain deprotection conditions.

In a typical procedure for the removal of a methyl hydroxy protecting group, a methoxyphenylsulphone of the formula (II) is treated with boron tribromide in a suitable organic solvent, e.g. dichloromethane, at room temperature.

A trialkylsilyl group can also be used as a hydroxy protecting group. The tert-butyidimethylsilyl group is preferred and it may be removed by treatment with fluoride ion, e.g. using tetrabutylammonium fluoride or hydrofluoric acid.

When the compound of the formula (I) to be prepared is a 1,2-diol, this can be prepared from a compound of the formula (II) where both hydroxy groups are protected together, e.g. as a ketal.

The compounds of the formula (II) where $R^3$ has the definition (a) as previously defined for $R^3$ for a compound of the formula (I) can be prepared from a compound of the formula (VI) by a similar procedure to that described in method (2) for the preparation of the compounds of the formula (I).

The compounds of the formula (II) where $R^3$ has the definition (b) or (c) as previously defined for $R^3$ for a compound of the formula (I) can be prepared by first converting a compound of the formula (VI) to the corresponding 4-amino-3-hydroxybenzopyran derivative by a similar procedure to that described for the preparation of a compound of the formula (VII) from a compound of the formula (III) in method (4), followed by further reaction thereof to incorporate the desired 4-substituent by a similar procedure to that described in any one or more of methods (4), (5) and (7), as appropriate.

2) The compounds of the formula (I) where $R^3$ has the definition (a) as previously defined for $R^3$ for a compound of the formula (I), and X, R, $R^1$, $R^2$ and $R^4$ are as previously defined for a compound of the formula (I), can be prepared by reaction of a compound of the formula:

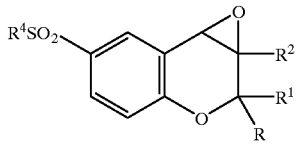

(III)

where R, $R^1$, $R^2$ and $R^4$ are as previously defined for this method, either with a compound of the formula:

$R^3XH$ or, where appropriate, a tautomer thereof, and in the presence of a base, or with a base salt of a compound of the formula:

$R^3XH$ where X and $R^3$ are as previously defined for this method.

Preferred base salts of the compounds of the formula $R^3XH$ include the alkali metal salts, e.g. the sodium and potassium salts. If a base salt is used, this may be generated in situ from the corresponding compound of the formula $R^3XH$ using a suitable base, e.g. sodium hydride.

If a base salt of the compound of the formula $R^3XH$ is not used, a suitable base, e.g. pyridine or triethylamine, must also be present although only a catalytic amount is usually necessary.

The reaction may be carried out in a suitable organic solvent, e.g. ethanol or 1,4-dioxane, at from room temperature to, and preferably at, the reflux temperature of the solvent.

The compounds of the formula (III) can be prepared by the following procedure:

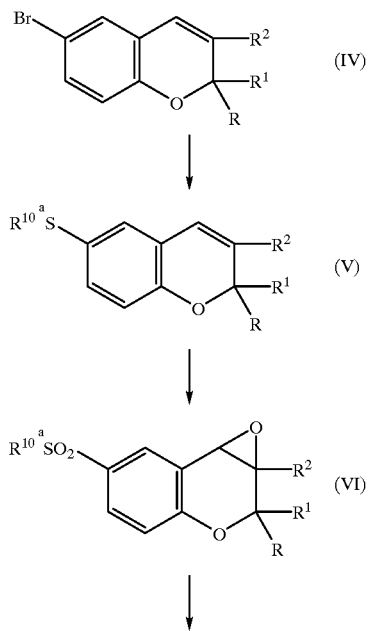

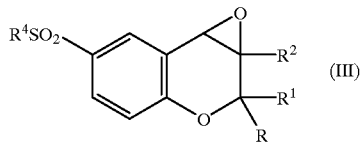

(III)

where $R^{10a}$ is phenyl substituted by a protected hydroxy group and optionally further substituted by 1 or 2 substituents each independently selected from a protected hydroxy group, $C_1$–$C_6$ alkyl, —$OR^5$, halo, cyano and nitro, and R, $R^1$, $R^2$, $R^4$ and $R^5$ are as previously defined for a compound of the formula (I) for method (2).

In a typical procedure, a compound of the formula (IV) is reacted with a thiol of the formula:

$R^{10a}SH$ where $R^{10a}$ is as previously defined for this method, in the presence of sodium t-butoxide and tetrakis (triphenylphosphine)palladium(0) in a suitable solvent, e.g. ethanol, and at the reflux temperature thereof.

The compound of the formula (V) produced can be converted to an oxirane of the formula (VI) by oxidation using sodium hypochlorite in the presence of [(R,R) or (S,S)-1,2-bis(3,5-di-tert-butylsalicylideamino)]cyclohexane manganese(III) chloride (see J.A.C.S., 1991, 113, 7063).

The hydroxy protecting group(s) can then be removed from a compound of the formula (VI) by a conventional procedure to provide a compound of the formula (III).

It is possible to prepare a compound of the formula (V) from a compound of the formula (IV) using methyl as the hydroxy protecting group in $R^{10a}$, to dealkylate this compound to provide the corresponding phenol and then to reprotect the phenol with a second hydroxy protecting group, e.g. benzyl, prior to carrying out the oxidation reaction.

All the compounds of the formulae (IV) and $R^{10a}SH$ can be prepared by conventional procedures.

3) The compounds of the formula (I) where $R^3$ has the definition (a) as previously defined for $R^3$ for a compound of the formula (I), and X, R, $R^1$, $R^2$ and $R^4$ are as previously defined for a compound of the formula (I), can be prepared by reaction of a compound of the formula:

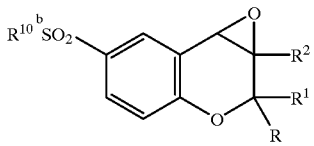

(VIA)

where $R^{10b}$ is phenyl substituted by a tri($C_1$–$C_4$ alkyl) silyloxy group (i.e. a tri($C_1$–$C_4$ alkyl)silyl protected hydroxy group) and optionally further substituted by 1 or 2 substituents each-independently selected from tri($C_1$–$C_4$ alkyl) silyl oxy, hydroxy, $C_1$–$C_6$ alkyl, —$OR^5$, halo, cyano, and nitro and R, $R^1$, $R^2$ and $R^5$ are as previously defined for a compound of the formula (I), either with a compound of the formula:

$R^3XH$ or, where appropriate, a tautomer thereof, and in the presence of a base, or with a base salt of a compound of the formula:

R³XH where X and R³ are as defined for this method.

A preferred tri($C_1$–$C_4$ alkyl)silyloxy protecting group is tert-butyldimethylsilyloxy.

Preferred base salts of the compounds of the formula R³XH include the alkali metal salts, e.g. the sodium and potassium salts. If a base salt is used, this may be generated in situ from the corresponding compound of the formula R³XH using a suitable base, e.g. sodium hydride.

If a base salt of a compound of the formula R³XH is not used, a suitable base, e.g. pyridine or triethylamine, must be present although only a catalytic amount is necessary.

In a typical procedure where a base salt of a compound of the formula R³XH is not used, the reaction is carried out in a suitable organic solvent, e.g. 1,4-dioxane, ethanol, isopropanol or diethylene glycol, and at an elevated temperature, e.g. at or about the reflux temperature of the solvent.

4) The compounds of the formula (I) where X is NH, R³ is a group of the formula:

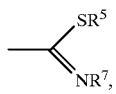

and R, R¹, R², R⁴, R⁵ and R⁷ are as previously defined for a compound of the formula (I), can be prepared by reaction of a compound of the formula:

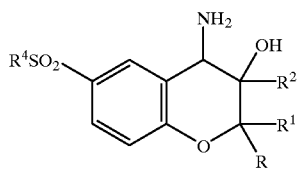

(VII)

where R, R¹, R² and R⁴ are as previously defined for this method, with a compound of the formula:

($R^5S$)₂C=NR⁷ where R⁵ and R⁷ are as previously defined for this method.

In a typical procedure the reactants are heated together in the presence of a base catalyst, e.g. pyridine, and in a suitable solvent, e.g. ethanol.

The compounds of the formula (VII) can be prepared by treatment of a compound of the formula (III) with a ethanolic solution of aqueous ammonia, typically at a temperature of from 40 to 50° C.

5) The compounds of the formula (I) where X is NH, R³ is a group of the formula:

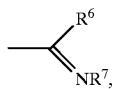

R⁶ is —OR⁵, —NHR⁵, —N(R⁵)₂ or —NHR⁹ and R, R¹, R², R⁴, R⁵, R⁷ and R⁹ are as previously defined for a compound of the formula (I), can be prepared by reaction of a compound of the formula (I) where X, R, R¹, R², R³, R⁴, R⁵ and R⁷ are as defined for method (4) for the preparation of compounds of the formula (I), with a suitable base salt of a compound of the formula R⁵OH (i.e. an alkoxide derivative), or with a compound of the formula R⁵NH₂, (R⁵)₂NH or R⁹NH₂, or a suitable base salt thereof, as appropriate, where R⁵ and R⁹ are as defined for this method.

Suitable base salts of the compounds of the formula R⁵OH, R⁵NH₂, (R⁵)₂NH and R⁹NH₂ include the alkali metal salts, e.g. the sodium and potassium salts.

The reaction is typically carried out in a suitable solvent, e.g. tetrahydrofuran, and at the reflux temperature thereof.

6) The compounds of the formula (I) where X is NH, R³ is a 6-membered heterocyclic ring containing 1 or 2 N heteroatoms which is optionally substituted as previously defined in definition (a) for R³ for a compound of the formula (I), and R, R¹, R² and R⁴ are as previously defined for a compound of the formula (I), can be prepared by reaction of a compound of the formula (VIII) where R, R¹, R² and R⁴ are as previously defined for a compound of the formula (VII), with a 6-membered ring heterocyclic compound containing 1 or 2 N heteroatoms which is substituted on a ring carbon atom by a leaving group, e.g. halo (preferably chloro or bromo) or a group of the formula ($C_1$–$C_4$ alkyl)S(O)$_n$— where n is 0, 1 or 2, and optionally further substituted as previously defined for R³ for this method.

In a typical procedure when a halo leaving group is used, the reaction is carried out in the presence-of-a suitable-acid acceptor, e.g. diisopropylethylamine, in a suitable solvent, e.g. 1,4-dioxane, and at the reflux temperature of the solvent.

7) The compounds of the formula (I) where X is NH, R³ is a group of the formula:

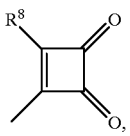

and R, R¹, R², R⁴ and R⁸ are as previously defined for a compound of the formula (I), can be prepared by reaction of a compound of the formula (VII) where R, R¹, R² and R⁴ are as previously defined for a compound of the formula (VII), with a compound of the formula:

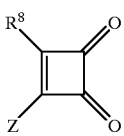

(VIII)

where Z is a suitable leaving group, e.g. ethoxy, and R⁸ is as previously defined for this method.

In a typical procedure the compounds are heated together in a suitable solvent, e.g. ethanol, and at about the reflux temperature thereof.

The compounds of the formula (VIII) may be prepared by conventional procedures.

All of the above reactions and the preparations of novel starting materials used in the preceding methods are conventional and appropriate reagents and reaction conditions for their performance or preparation as well as procedures for isolating the desired products are well known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or is recovered by evaporation of the solvent.

The compounds of the formula (I) have smooth muscle relaxant activity since they are able to open potassium channels in such tissue. They can be tested for smooth muscle relaxant activity by a method involving measuring the in vitro relaxation of electrically stimulated guinea pig tracheal rings as follows.

Adult male guinea pigs (Porcellus, 500–900 g) were killed by a blow to the head with subsequent exsanguination. Each trachea was excised and placed in Krebs solution (the composition of the Krebs solution was as follows (millimoles): NaCl (119); KCl (4.7); $NaHCO_3$ (25); $KH_2PO_4$ (1.2); $MgSO_4$ (1.2); $CaCl_2$ (2.5); glucose (11), and indomethacin (2.8 μM) was added to remove the influence of the endogenous prostanoids: the solution was gassed with 95% oxygen/5% carbon dioxide and the temperature was kept constant at 37° C.). The adherent connective tissue was dissected away and the tracheal tube opened by cutting through the cartilage on the side opposite to the smooth muscle band. A long cotton thread was attached to the cartilage at one end of the tracheal strip for attachment to an isometric transducer and another thread was attached to the other end of the strip for connection to a stimulation electrode. The preparation was mounted under a resting tension of 1 g in a 15 ml organ bath which was maintained at 37° C. and gassed with 95% oxygen/5% carbon dioxide. The tissue was washed at 15 minute intervals and allowed to equilibrate for 1 hour.

At the end of the equilibration period the tissue was stimulated at a frequency of 1 Hz, pulse duration of 0.1 ms and at a supramaximal voltage of 25–30 V for a period of 10 seconds at 100 second intervals. When the contractile responses had stabilised, a single concentration of a compound of the formula (I), or a pharmaceutically acceptable salt thereof, was added to the bath and stimulation of the tissues was continued for 2 hours.

The minimum dose of the compound of the formula (I) which causes maximal inhibition of the cholinergic contraction relative to control was then determined.

For human use, the compounds of the formula (I) and their salts can be administered alone, but will generally be administered in admixture with a pharmaceutical carrier selected with regard to the intended route of administration and standard pharmaceutical practice.

For example, they can be administered orally in the form of tablets containing such excipients as starch or lactose, or in capsules or ovules either alone or in admixture with excipients, or in the form of elixirs, solutions or suspensions containing flavouring or colouring agents.

They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses) and preferably will be from 0.1 to 5 mg/kg.

Thus tablets or capsules of the compounds will contain from 1 mg to 0.5 g of active compound for administration singly or two or more at a time, as appropriate. The physician in any event will determine the actual dosage which will be most suitable for an individual patient and It will vary with the age, weight and response of the. particular patient. The above dosages are exemplary of the average case; there can, of course, be individual instances where higher or lower dosage ranges are merited, and such are within the scope of this invention.

The compounds of formula (I) can also be administered by inhalation and are conveniently delivered in the form of an aerosol spray presentation from a pressurised container or a nebuliser with the use of a suitable propellant, e.g. dichlorodifluoromethane, trichlorofluoromethane, dichlorotetrafluoroethane, a hydrofluoroalkane, carbon dioxide or other suitable gas. In the case of a pressurised aerosol, the dosage unit may be determined by providing a valve to deliver a metered amount. The pressurised container or nebuliser may contain a solution or suspension of the active compound. Administration by inhalation may also be carried out using a dry powder inhaler. Capsules and cartridges (made, for example, from gelatin) for use in an inhaler or insufflator may be formulated to contain a powder mix of a compound of formula (I) and a suitable powder base such as lactose or starch.

Aerosol formulations are preferably arranged so that each metered dose or "puff" of aerosol contains from 20 μg to 1000 μg of a compound of formula (I), or a pharmaceutically acceptable salt thereof, for delivery to the patient. The overall daily dose with an aerosol will be within the range of from 20 μg to 10 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration of from 1 to 10%, into an ointment consisting of a white wax or white soft paraffin base together with such stabilizers and preservatives as may be required.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the curative or prophylactic treatment of a disease associated with the altered tone and/or motility of smooth muscle;

iv) use as stated in (iii) where the disease is chronic obstructive airways disease, asthma, urinary incontinence, irritable bowel syndrome, diverticular disease, oesophageal achalasia or hypertension;

v) a method of treatment of a human to cure or prevent a disease associated with the altered tone and/or motility of smooth muscle which comprises treating said human with an effective amount of a compound of the formula (I) or with a pharmaceutically acceptable salt or composition thereof;

vi) a method as stated in (v) where the disease is chronic obstructive airways disease, asthma, urinary incontinence, irritable bowel syndrome, diverticular disease, oesophageal achalasia or hypertension; and vii) intermediates of the formulae (II), (III), (VIA) and (VII).

The following Examples illustrate the preparation of the compounds of the formula (I):

EXAMPLE 1

(3S,4R)-4-(2-Chloropyrimidin-4-yl)amino-3,4-dihydro-3-hydroxy-6-(3-hydroxyphenyl)sulphonyl-2,2,3-trimethyl-2H-benzo[b]pyran

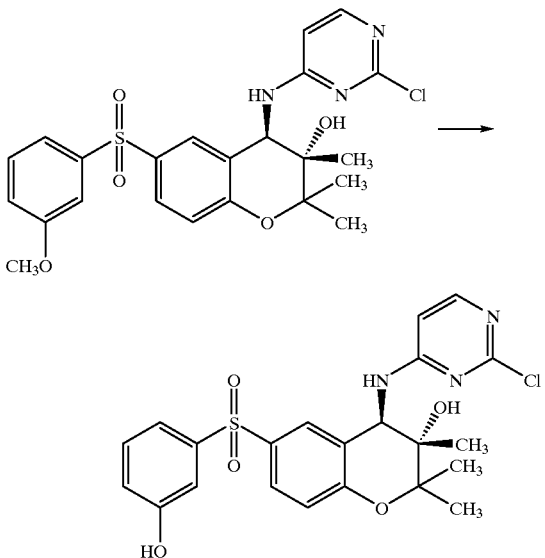

(3S,4R)-4-(2-Chloropyrimidin-4-yl)amino-3,4-dihydro-3-hydroxy-6-(3-methoxyphenyl)sulphonyl-2,2,3-trimethyl-2H-benzo[b]pyran (0.23 g) (see Preparation 19) was dissolved in dichloromethane (25 ml) (the flask was fitted with a calcium chloride drying tube) and boron tribromide (1 ml) was added. The mixture was stirred at room temperature for 24 hours and a precipitate was formed. The dichloromethane was decanted off, the solid taken up in 1N aqueous sodium hydroxide and washed with ethyl acetate. The aqueous phase was acidified to give a gum which was collected and dried under reduced pressure at 70° C. to yield (3S,4R)-4-(2-chloropyrimidin-4-yl)amino-3,4-dihydro-3-hydroxy-6-(3-hydroxyphenyl)sulphonyl-2,2,3-trimethyl-2H-benzo[b]pyran (0.123 g) as a white solid, m.p.>280° C. LRMS m/z=475 (m)⁺.

$^1$H-NMR (d$_6$-DMSO): δ=10.20(1H,s), 8.15(1H,d), 8.05 (1H,d), 7.65(1H,m), 7.50(1H,d), 7.15–7.40(3H,m), 7.00(2H, m), 6.75(1H,d), 5.50(1H,d), 1.40(3H,s), 1.30(3H,s), 1.10 (3H,s) ppm.

EXAMPLE 2

(3S,4R)-3,4-Dihydro-4-(3,4-dioxo-2-ethoxycyclobut-1-en-1-yl)amino-3-hydroxy-6-(3-hydroxyphenyl)sulphonyl-2,2,3-trimethyl-2 H-benzo[b]pyran

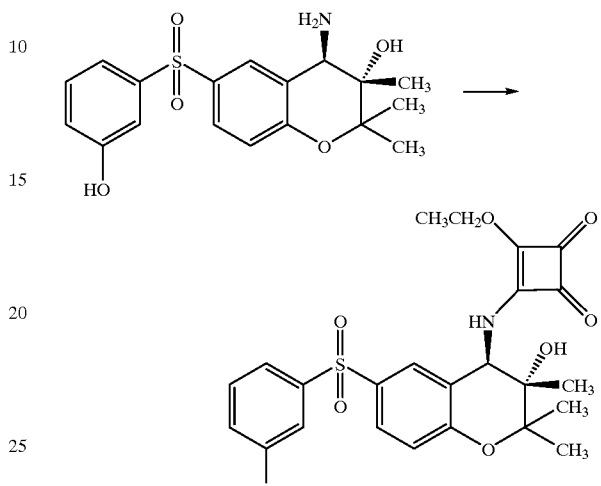

(3S,4R)-4-Amino-3,4-dihydro-3-hydroxy-6-(3-hydroxyphenyl)-sulphonyl-2,2,3-trimethyl-2H-benzo[b] pyran (0.62 g) (see Preparation 20) and 1,2-diethoxy-3,4-dioxocyclobut-1-ene (0.15 g) were dissolved in ethanol (10 ml) (a calcium chloride drying tube was attached to the flask) and the mixture was heated under reflux for 90 minutes. The solvent was removed under reduced pressure, the residue was then azeotroped with dichloromethane and the crude product was chromatographed on silica with 5:95 methanol:dichloromethane as the eluent to yield (3S,4R)-3, 4-dihydro-4-(3,4-dioxo-2-ethoxycyclobut-1-en-1-yl)amino-3-hydroxy-6-(3-hydroxyphenyl)sulphonyl-2,2,3-trimethyl-2H-benzo[b]pyran (0.3 g) as a yellow solid.

$^1$H-NMR (d$_6$-DMSO) (two rotamers observed): δ=10.20 (1H, broad), 9.25(0.5H,broad), 9.00(0.5H,broad), 7.75(2H, m), 7.38(2H,m), 7.25(1H,s), 7.00(2H,m), 5.45(0.5H,d), 5.38 (0.5H,s), 5.30(0.5H,s), 4.95(1H,d), 4.75(1H,q), 4.60 (1H, broad), 1.45(1.5H,t), 1.38(3H,s), 1.29(1.5H,broad), 1.22 (3H,s), 0.99(3H,s) ppm.

EXAMPLE 3

(3S,4R)-4-(3-Cyano-2-methylisothioureido)-3,4-dihydro-3-hydroxy-6-(3-hydroxyphenyl)sulphonyl-2,2,3-trimethyl-2H-benzo[b]pyran

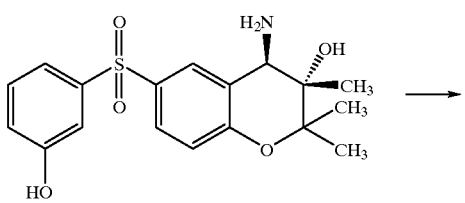

-continued

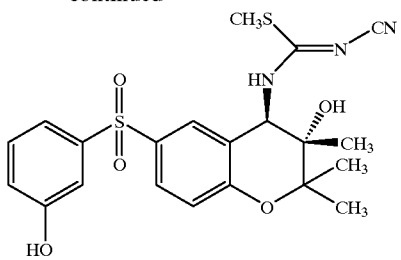

(3S,4R)-4-Amino-3,4-dihydro-3-hydroxy-6-(3-hydroxyphenyl)-sulphonyl-2,2,3-trimethyl-2H-benzo[b]pyran (0.6 g) (see Preparation 20) and dimethyl N-cyanodithioiminocarbonate (0.24 g) were dissolved in pyridine (10 ml) (a calcium chloride drying tube-was attached to the flask) and the mixture heated at 50–60° C. for 24 hours. The solvent was removed under reduced pressure and the residue chromatographed on silica with 1:1 ethyl acetate:dichloromethane as the eluent to give a crude product which was azeotroped with ethyl acetate followed by dichloromethane, and then triturated with diethyl ether (to remove residual pyridine) to yield (3S,4s)-4-(3-cyano-2-methylisothioureido)-3,4-dihydro-3-hydroxy-6-(3-hydroxyphenyl)sulphonyl-2,2,3-trimethyl-2H-benzo[b]pyran (0.276 g) as a solid.

$^{1}$H-NMR (d$_{6}$-DMSO): δ=10.25(1H,s), 8.50(1H,d), 7.70(1H,d), 7.50(1H,s), 7.30–7.45(2H,m), 7.25(1H,d), 6.98–7.05(2H,m), 5.45(1H,d), 5.40(1H,s), 2.72(3H,s), 1.37 (3H,s), 1.25(3H,s), 1.07(3H,s) ppm.

EXAMPLE 4

(3S,4R)-3,4-Dihydro-3-hydroxy-6-(4-hydroxyphenyl)sulphonyl-4-hydroxypyridazin-6-yl)oxy-2,2,3-trimethyl-2H-benzo[b]pyran

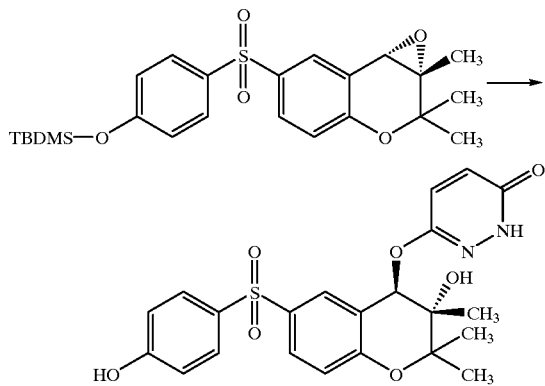

(3S,4S)-6-(4-tert-Butyldimethylsilyloxyphenyl)sulphonyl-3,4-dihydro-3,4-epoxy-2,2,3-trimethyl-2H-benzo[b]pyran (0.35 g) (see Preparation 14) and 3,6-dihydroxypyridazine (0.273 g) were suspended in absolute ethanol (3 ml), dry pyridine (0.065 ml) was added and the mixture was heated under reflux for 4 days. The solvent was then removed under reduced pressure and the residue chromatographed on silica with 1:99 methanol:ethyl acetate as the eluent to yield (3S,4R)-3,4-dihydro-3-hydroxy-6-(4-hydroxyphenyl)sulphonyl-4-(3-hydroxypyridazin-6-yl)oxy-2,2,3-trimethyl-2H-benzo[b]pyran (0.155 g) as a white solid, m.p. >200° C. Found: C,57.54; H,5.35; N,5.57. C$_{22}$H$_{22}$N$_{2}$O$_{7}$S, 0.20 ethyl acetate requires C,57.50; H,4.99; N,5.88%.

$^{1}$H-NMR (d$_{6}$-DMSO): δ=12.38(1H,s), 7.16(4H,m), 7.25(1H,d), 6.80–7.00(4H,m), 5.80(1H,s), 5.38(1H,s), 1.38(3H,s), 1.30 (3H,s), 1.15(3H,s) ppm.

EXAMPLE 5

(3S,4R)-3,4-Dihydro-4-(2,3-dihydro-2-methyl-3-oxopyridazin-6-yl)oxy-3-hydroxy-6-(4-hydroxyphenyl)sulphonyl-2,2,3-trimethyl-2H-benzo[b]pyran

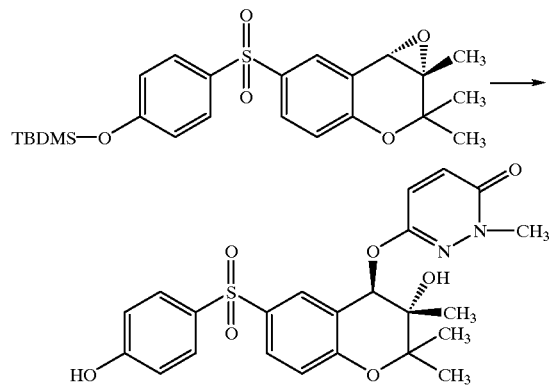

(3S,4S)-6-(4-tert-Butyldimethylsilyloxyphenyl)sulphonyl-3,4-dihydro-3,4-epoxy-2,2,3-trimethyl-2H-benzo[b]pyran (1.618 g) (see Preparation 14) and 2,3-dihydro-2-methyl-3-oxo-6-hydroxypyridazin (1.33 g) (see J.Org.Chem, 1971, 36, 3372) were suspended in dry 1,4-dioxane (15 ml), pyridine (0.275 ml) was added and the mixture was heated under reflux (a calcium chloride drying tube was attached to the flask) for 3 days. The solvent was removed under reduced pressure and the residue was partitioned between ethyl acetate and water. The organic phase was separated and dried (anhydrous sodium sulphate), the solvent was removed under reduced pressure and the crude product was chromatographed on silica using 1:99 methanol:ethyl acetate as the eluent to yield (3S,4R)-3,4-dihydro-4-(2,3-dihydro-2-methyl-3-oxopyridazin-6-yl)oxy-3-hydroxy-6-(4-hydroxyphenyl)sulphonyl-2,2,3-trimethyl-2H-benzo[b]pyran (0.352 g) as a white solid. Found: C,58.13; H,5.00; N,5.70. C$_{23}$H$_{24}$N$_{2}$O$_{7}$S requires C,58.46; H,5.12; N,5.93%.

$^{1}$H-NMR (d$_{6}$-DMSO): δ=7.65–7.75(4H,m), 7.27(1H,d), 6.82–7.05(4H,m), 5.78(1H,s), 5.36(1H,s), 3.34(3H,s), 1.39 (3H,s), 1.30(3H,s), 1.20(3H,s) ppm.

EXAMPLE 6

(3S,4R)-3,4-Dihydro-4-(2,3-dihydro-2-ethyl-3-oxopyridazin-6-yl)oxy-3-hydroxy-6-(4-hydroxyphenyl)sulphonyl-2,2,3-trimethyl-2H-benzo[b]pyran

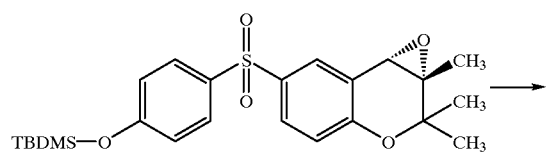

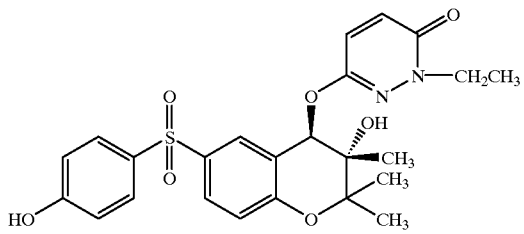

(3S,4S)-6-(4-tert-Butyldimethylsilyloxyphenyl)sulphonyl-3,4-dihydro-3,4-epoxy-2,2,3-trimethyl-2H-benzo[b]pyran (1.664 g) (see Preparation 14) and 2,3-dihydro-2-ethyl-3-oxo-6-hydroxypyridazin (1.52 g) (see J.Org.Chem, 1971, 36, 3372) were suspended in dry 1,4-dioxane (15 ml), pyridine (0.282 ml) was added and the mixture was heated under reflux (a calcium chloride drying tube was attached to the flask) for 3 days. The solvent was removed under reduced pressure and the residue was partitioned between ethyl acetate and water. The organic phase was separated and dried (anhydrous sodium sulphate), the solvent removed under reduced pressure and the crude product was chromatographed on silica with 1:99 methanol:ethyl acetate as the eluent to yield (3S,4R)-3,4-dihydro-4-(2,3-dihydro-2-ethyl-3-oxopyridazin-6-yl)oxy-3-hydroxy-6-(4-hydroxyphenyl)-sulphonyl-2,2,3-trimethyl-2H-benzo[b]pyran (0.340 g) as a white solid, m.p. 186–188° C.

Found: C,59.16; H,5.27; N,5.10. $C_{24}H_{26}N_2O_7S$, 0.10 ethyl acetate requires C,59.16; H,5.45; N,5.65%.

$^1$H-NMR (CDCl$_3$): δ=7.52–7.70(4H,m), 7.16(1H,d), 6.72–6.98 (4H,m), 5.72(1H,s), 5.30(1H,s), 4.97(1H,m), 4.80 (1H,m), 1.28(3H,s), 1.18(6H,m), 1.08(3H,s) ppm.

EXAMPLE 7

(3S,4R)-3,4-Dihydro-4-(2,3-dihydro-2-methyl-3-oxopyridazin-6-yl)oxy-3-hydroxy-6-(3-hydroxyphenyl)sulphonyl-2,2,3-trimethyl-2 H-benzo[b]pyran

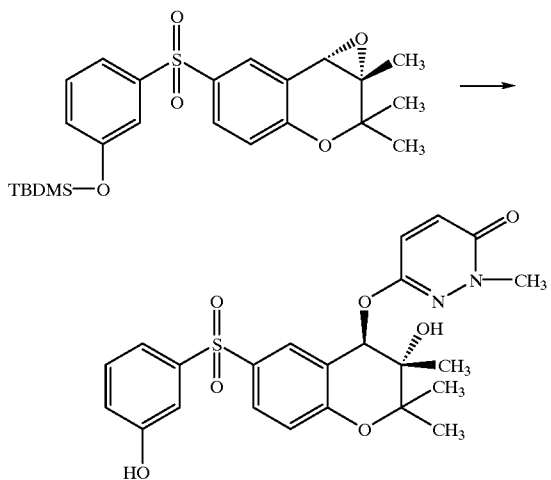

(3S,4S)-6-(3-tert-Butyldimethylsilyloxyphenyl)sulphonyl-3,4-dihydro-3,4-epoxy-2,2,3-trimethyl-2H-benzo[b]pyran (2.0 g) (see Preparation 15) and 2,3-dihydro-2-methyl-3-oxo-6-hydroxypyridazin (1.5 g) (see J.Org.Chem, 1971, 36, 3372) were suspended in ethanol (30 ml), pyridine (0.31 g) was added and the mixture was heated under reflux (a calcium chloride drying tube was attached to the flask) for 100 hours. After cooling the reaction was filtered and the filtrate was evaporated to yield a solid-which was dissolved in 0.5% methanol/dichloromethane and filtered again. The filtrate was again evaporated and the residue was chromatographed on silica eluting with a solvent gradient of 0.5:99.5 to 3.75:96.25 methanol:dichloromethane to yield (3S,4R)-3,4-dihydro-4-(2,3-dihydro-2-methyl-3-oxo-pyridazinyl-6-yl)oxy-3-hydroxy-6-(3-hydroxyphenyl)sulphonyl-2,2,3-trimethyl-2H-benzo[b]pyran (1.0 g) as a white solid. Found: C,53.20; H,4.79; N,5.22.

$C_{23}H_{24}N_2O_7S$, 0.75 $CH_2Cl_2$ requires C,53.00; H,4.79; N,5.10%. $^1$H-NMR (CDCl$_3$): δ=8.04(1H,s), 7.75–7.85(2H, m), 7.30–7.45 (3H,m), 6.90–7.10(4H,m), 5.91(1H,s), 3.72 (3H,s), 3.32 (1H,s), 1.45(3H,s), 1.40(3H,s), 1.30(3H,s) ppm.

EXAMPLE 8

(3S,4R)-3,4-Dihydro-4-(2,3-dihydro-2-methyl-3-oxopyridazin-6-yl)oxy-3-hydroxy-6-(2-hydroxyphenyl)sulphonyl-2,2,3-trimethyl-2H-benzo[b]pyran

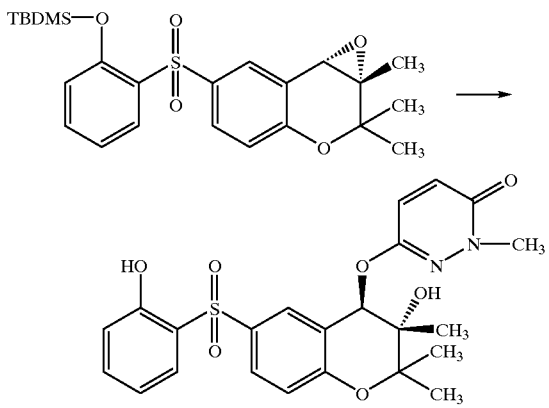

(3S,4S)-6-(2-tert-Butyldimethylsilyloxyphenyl)sulphonyl-3,4-dihydro-3,4-epoxy-2,2,3-trimethyl-2H-benzo[b]pyran (0.5 g) (see Preparation 16) and 2,3-dihydro-2-methyl-3-oxo-6-hydroxypyridazin (0.41 g) (see J.Org.Chem., 1971, 36, 3372) were suspended in dry 1,4-dioxane (8 ml), pyridine (0.085 g) was added and the mixture was heated under reflux (a calcium chloride drying tube was attached to the flask) for 20 hours. The solvent was removed under reduced pressure, the residue was stirred with dichloromethane (30 ml) and filtered. The filtrate was evaporated and the residue was chromatographed on silica using 1:1 hexane:ethyl acetate as the eluent to yield a mixture of the required product and the epoxide starting material. This mixture was redissolved in dry 1,4-dioxane (7 ml), 2,3-dihydro-2-methyl-3-oxo-6-hydroxypyridazin (0.2 g) and pyridine (0.08 g) were added and the reaction was heated under reflux for a further 18 hours. The solvent was removed under reduced pressure and the residue was dissolved in 5% methanol/dichloromethane and filtered. The filtrate was evaporated and the residue was chromatographed on silica using 2.5:97.5 methanol:dichloromethane as the eluent to yield (3S,4R)-3,4-dihydro-4-(2,3-dihydro-2-methyl-3-oxopyridazin-6-yl)oxy-3-hydroxy-6-(2-hydroxyphenyl)-sulphonyl-2,2,3-trimethyl-2H-benzo[b]pyran (0.17 g) as a yellow foam. Found: C,54.19; H,4.85; N,5.21. $C_{23}H_{24}N_2O_7S$, 0.625 $CH_2Cl_2$ requires C,54.06; H,4.73; N,5.34%.

$^1$H-NMR (CDCl$_3$): δ=9.15(1H,s), 7.90(1H,d), 7.75(1H, dd), 7.62(1H,dd), 7.45(1H,m), 6.94–7.10(5H,m), 5.89(1H, s), 3.69(1H,s), 3.48(1H,s), 1.51(3H,s,), 1.42(3H,s), 1.25(3H, s) ppm.

EXAMPLE 9

(3S,4R)-3,4-Dihydro-4-(1,2-dihydro-1-oxo-2H-1phthalazin-4-yl)oxy-3-hydroxy-6-(4-hydroxyphenyl)sulphonyl-2,2,3-trimethyl-2H-benzo[b]pyran

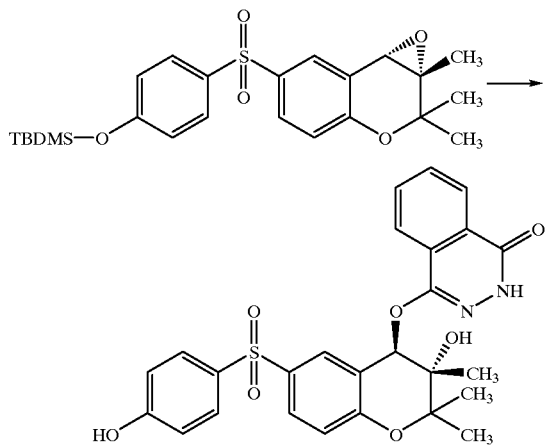

A mixture of (3S,4S)-6-(4-tert-butyldimethylsilyloxyphenyl)sulphonyl-3,4-dihydro-3,4-epoxy-2,2,3-trimethyl-2H-benzo[b]pyran (0.81 g) (see Preparation 14), phthalhydrazide (0.88 g), pyridine (0.5 ml) and diethylene glycol (10 ml) was heated at 120° C. for 210 minutes. The reaction mixture was poured into water and extracted with ethyl acetate. The organic extract was dried (anhydrous magnesium sulphate), the solvent was evaporated and the resultant gum was chromatographed on silica using 180:20:1 dichloromethane:methanol:35% aqueous ammonia solution as the eluent to yield (3S,4R)-3,4-dihydro-4-(1,2-dihydro-1-oxo-2H-phthalazin-4-yl)oxy-3-hydroxy-6-(4-hydroxyphenyl)sulphonyl-2,2,3-trimethyl-2H-benzo[b]pyran (0.091 g) as a solid.

$^1$H-NMR (d$_6$-DMSO): δ=8.28(1H,d), 7.80–7.95(4H,m), 7.55–7.70(3H,m), 6.95(1H,d), 6.90(1H,d), 6.80(1H,d), 5.41 (1H,s), 1.50(3H,s), 1.38(3H,s), 1.28(3H,s) ppm.

EXAMPLE 10

(3S,4R)-3,4-Dihydro-4-(1,2-dihydro-2-methyl-1-oxophthalazin-4-yl)oxy-3-hydroxy-6-(4-hydroxyphenyl)sulphonyl-2,2,3-trimethyl-2H-benzo[b]pyran

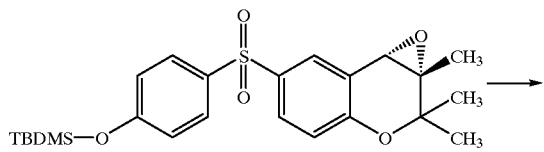

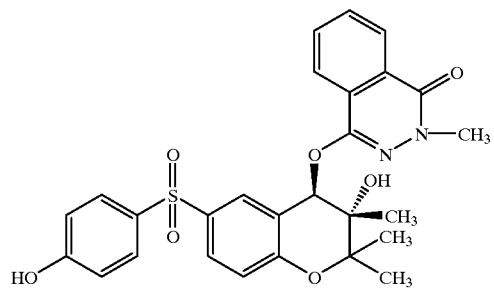

A mixture of (3S,4S)-6-(4-tert-butyldimethylsilyloxyphenyl)sulphonyl-3,4-dihydro-3,4-epoxy-2,2,3-trimethyl-2H-benzo[b]pyran (0.71 g) (see Preparation 14), 1,2-dihydro-4-hydroxy-2-methyl-1-oxophthalazin (0.846 g) (see Preparation 21), pyridine (0.4 ml) and 1,4-dioxane (10 ml) was heated under reflux for 4 days. The solvent was removed under reduced pressure, the residue was dissolved in ethyl acetate and washed first with dilute aqueous citric acid solution and then with brine. The organic phase was dried (anhydrous magnesium sulphate), the solvent was removed and the crude product was chromatographed on silica eluting with a solvent gradient of 100:1:0.15 to 180:20:1 dichloromethane:methanol:35% aqueous ammonia solution to yield (3S,4R)-3,4-dihydro-4-(1,2-dihydro-2-methyl-1-oxophthalazin-4-yl)oxy-3-hydroxy-6-(4-hydroxyphenyl)sulphonyl-2,2,3-trimethyl-2H-benzo[b]pyran (0.12 g) as a solid.

$^1$H-NMR (CDCl$_3$): δ=8.40(1H,d), 8.26(1H,s), 7.78–7.95 (5H,m), 7.68(2H,d) 6.95(1H,d), 6.90(2H,d), 6.09(1H,s), 3.73(3H,s), 1.60(3H,s), 1.50(3H,s), 1.32(3H,s) ppm.

EXAMPLE 11

(3S,4R)-3,4-Dihydro-4-(1,2-dihydro-2-oxo-1H-pyridin-4-yl)oxy-3-hydroxy-6-(3-hydroxyphenyl)sulphonyl-2,2,3-trimethyl-2H-benzo[b]pyran

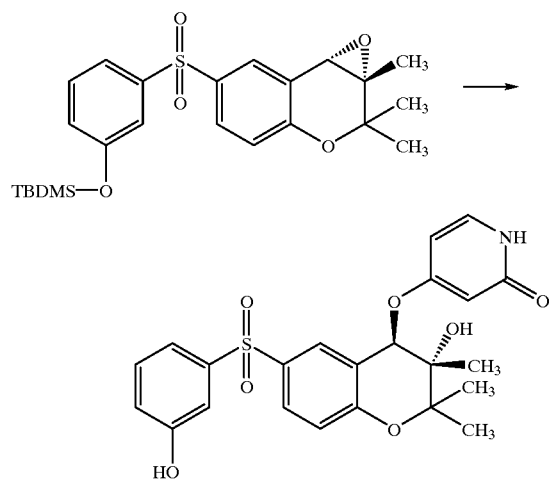

(3S,4S)-6-(3-tert-Butyldimethylsilyloxyphenyl) sulphonyl-3,4-dihydro-3,4-epoxy-2,2,3-trimethyl-2H-benzo[b]pyran (0.70 g) (see Preparation 15) and 2,4-dihydroxypyridazine (0.44 g) were suspended in ethanol (15 ml), pyridine (0.15 g) was added and the mixture was heated under reflux (a calcium chloride drying tube was attached to the flask) for 5 days. The solvent was removed under reduced pressure, the residue was stirred with 5% methanol/dichloromethane and then filtered. The filtrate was evaporated and the residue was chromatographed on silica using 19:1 dichloromethane:methanol as the eluent to yield first (3S,4R)-3,4-dihydro-4-(1,2-dihydro-2-oxo-1H-pyridin-4-yl)oxy-3-hydroxy-6-(3-hydroxyphenyl)sulphonyl-2,2,3-trimethyl-2H-benzo[b]pyran (0.118 g) as a white foam. Found: C,60.58; H,5.04; N,2.67. $C_{23}H_{23}NO_7S$, 0.30 diethyl ether requires C,60.60; H,5.46; N,2.92%.

$^1$H-NMR ($d_6$-DMSO): δ=10.20(1H,broad), 7.71 (1H,dd), 7.62 (1H,s), 7.30–7.40(2H,m), 7.25(1H,dd), 7.15(1H,d), 6.95–7.05(2H,m), 6.20(1H,s), 6.06(1H,dd), 5.45(1H,s), 5.40 (1H,s), 1.38(3H,s), 1.34(3H,s), 1.10(3H,s) ppm.

Further elution then provided (3S,4R)-3,4-dihydro-4-(1,2-dihydro-2-oxo-4-hydroxypyridazin-1-yl)-3-hydroxy-6-(3-hydroxyphenyl)sulphonyl-2,2,3-trimethyl-2H-benzo[b]pyran (0.142 g) as a foam.

$^1$H-NMR ($d_6$-DMSO): δ=10.50(1H,broad), 7.96(1H,d), 7.62–7.72(2H,m), 7.35(1H,m), 7.20(1H,d), 7.10(1H,s), 6.94–7.00 (2H,m), 6.65(1H,dd), 6.20(2H,m), 5.50(1H,s), 1.40(3H,s), 1.32(3H,s), 1.15(3H,s) ppm.

EXAMPLE 12

(3S,4R)-3,4-Dihydro-4-(1,2-dihydro-5.6-dimethyl-2-oxo-1H-pyridin-4-yl)oxy-3-hydroxy-6-(3-hydroxyphenyl)sulphonyl-2,2,3-trimethyl-2H-benzo[b]pyran

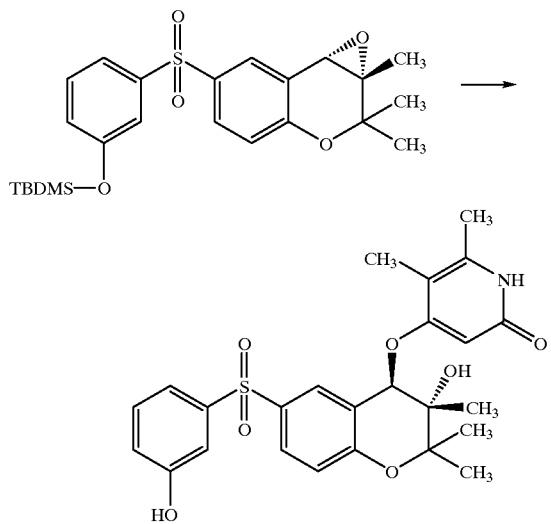

(3S,4S)-6-(3-tert-Butyldimethylsilyloxyphenyl)sulphonyl-3,4-dihydro-3,4-epoxy-2,2,3-trimethyl-2H-benzo[b]pyran (0.70 g) (see Preparation 15) and 2,4-dihydroxy-5,6-dimethylpyridine (0.42 g) (see Preparation 23) were suspended in ethanol (15 ml) and pyridine (0.12 g) was added. The mixture was heated under reflux (a calcium chloride drying tube was attached to the flask) for 20 days. The solvent was removed under reduced pressure, the residue was stirred in 20% methanol/dichloromethane (50 ml), filtered and the filtrate was evaporated to yield a crude product which was chromatographed on silica eluting with a solvent gradient of 19:1 to 9:1 dichloromethane:methanol to yield (3S,4R)-3,4-dihydro-4-(1,2-dihydro-5,6-dimethyl-2-oxo-1H-pyridin-4-yl)oxy-3-hydroxy-6-(3-hydroxyphenyl)sulphonyl-2,2,3-trimethyl-2H-benzo[b]pyran (0.143 g) as a solid.

$^1$H-NMR ($d_6$-DMSO): δ=10.30(1H,s), 6.96–7.85(8H,m), 6.18 (1H,s), 5.45(1H,s), 5.36(1H,s), 2.20(3H,s), 1.84(3H,s), 1.38(3H,s), 1.33(3H,s), 1.12(3H,s) ppm.

EXAMPLE 13

(3S,4R)-3,4-Dihydro-4-(2,3-dihydro-2-methyl-3-oxopyridazin-6-yl)oxy-6-(3,4-dihydroxyphenyl)sulphonyl-3-hydroxy-2,2,3-trimethyl-2H-benzo[b]pyran

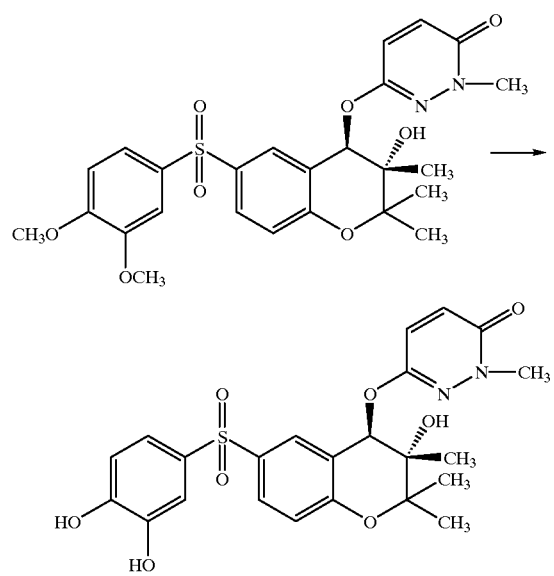

(3S,4R)-3,4-Dihydro-4-(2,3-dihydro-2-methyl-3-oxopyridazin-6-yl)oxy-6-(3,4-dimethoxyphenyl)sulphonyl-3-hydroxy-2,2,3-trimethyl-2H-benzo[b]pyran (0.50 g) (see Preparation 26) was dissolved in dichloromethane (12 ml) (under a nitrogen atmosphere) and boron tribromide (4 ml of a 1 M solution in dichloromethane) was added. The mixture was stirred at room temperature for one hour and a precipitate was formed. Water (20 ml) and dichloromethane (15 ml) were added, an insoluble gum formed and the solvents were decanted off. The gum was then chromatographed on silica using 1:9 methanol:dichloromethane as the eluent to yield (3S,4R)-3,4-dihydro-4-(2,3-dihydro-2-methyl-3-oxopyridazin-6-yl)oxy-6-(3,4-dihydroxyphenyl)sulphonyl-3-hydroxy-2,2,3-trimethyl-2H-benzo[b]pyran (0.33 g) as a white foam which was then triturated with diethyl ether and dried to give a white solid.

$^1$H-NMR ($d_6$-DMSO): δ=10.10(1H,s), 9.75(1H,s), 7.75 (1H,s), 7.65(1H,m), 7.30(1H,d), 7.15(2H,m), 7.05(1H,d), 6.95(1H,d), 6.85(1H,d), 5.80(1H,s), 5.72(1H,s), 3.60(3H,s), 1.40(3H,s), 1.31(3H,s), 1.15(3H,s) ppm.

The following Preparations illustrate the preparation of certain starting materials used in the preceding Examples.

PREPARATION 1

4-Bromophenyl propionate

4-Bromophenol (259 g) and 4-dimethylaminopyridine (1.5 g) were dissolved in dichloromethane (1000 ml), the solution was cooled in an ice bath and triethylamine (219 ml) was added portionwise such that the reaction temperature was kept below 20° C. Propionyl chloride (137 ml) was then added over 1 hour and the resulting mixture was stirred at room temperature for 2 hours. The mixture was washed with water followed by brine, then dried (anhydrous magnesium sulphate) and the solvent removed under reduced pressure to yield 4-bromophenyl propionate (344 g) as a green oil.

$^1$H-NMR (CDCl$_3$): δ=7.43(2H,d), 6.94(2H,d), 2.52(2H, q), 1.20(3H,t) ppm.

PREPARATION 2

1-(5-Bromo-2-hydroxyphenyl)propane-1-one

4-Bromophenyl propionate (115 g) (see Preparation 1) and aluminium chloride (150 g) were heated together at approximately 90° C. for 15 minutes. The solution became dark and hydrogen chloride gas was evolved. After cooling the black mass was carefully added to ice and a brown solid formed. The mixture was extracted with dichloromethane. The organic extract was separated, washed with brine, dried (anhydrous magnesium sulphate) and the solvent removed under reduced pressure to yield 1-(5-bromo-2-hydroxyphenyl)propane-1-one (110 g) as a yellow solid.

$^1$H-NMR (CDCl$_3$): δ=12.28(1H,s), 7.88(1H,d), 7.55(1H, dd), 6.89(1H,d), 3.02(2H,q), 1.27(3H,t) ppm.

PREPARATION 3

6-Bromo-3,4-dihydro-4-oxo-2,2,3-trimethyl-2H-benzo[b]pyran 1-(5-Bromo-2-hydroxyphenyl)propane-1-one (375 g) (see Preparation 2) was dissolved in a mixture of dry toluene (1700 ml) and acetone (2040 ml). Piperidine (748 ml) was added and the solution was heated under reflux for 7 days. The solvent was removed under reduced pressure, the residue was dissolved in diethyl ether and washed sucessively with aqueous citric acid solution (×4), 0.5M aqueous sodium hydroxide solution (×4) and then brine (×3). The organic phase was separated and the solvent was removed under reduced pressure to yield 6-bromo-3,4-dihydro-4-oxo-2,2,3-trimethyl-2H-benzo[b]pyran (408 g) as an orange oil. Found: C,53.59; H,4.84. C$_{12}$H$_{13}$BrO$_2$ requires G,53.55; H,4.87%.

$^1$H-NMR (CDCl$_3$): δ=7.90(1H,d), 7.50(1H,dd), 6.79(1H, d), 2.70(1H,q), 1.50(3H,s), 1.28(3H,s), 1.17(3H,s) ppm.

PREPARATION 4

6-Bromo-2,2,3-trimethyl-2H-benzo[b]pyran

6-Bromo-3,4-dihydro-4-oxo-2,2,3-trimethyl-2H-benzo[b]pyran (407 g) (see Preparation 3) was dissolved in ethanol (1500 ml), cooled in an ice bath and sodium borohydride (61.4 g) was added portionwise over 20 minutes. The mixture was stirred at room temperature for 3 hours, the solvent removed under reduced pressure, the residue dissolved in diethyl ether and the mixture washed first with water and then with brine. The organic layer was dried (anhydrous magnesium sulphate) and the solvent removed to yield the crude alcohol. This was dissolved in toluene (1000 ml), para-toluenesulphonic acid (40 g) added and the mixture heated under reflux (with removal of water) for 2 hours. The solvent volume was reduced to approximately 500 ml and the solution was washed with aqueous sodium carbonate solution and then brine. The organic phase was dried (anhydrous magnesium sulphate) and the solvent removed under reduced pressure to yield 6-bromo-2,2,3-trimethyl-2H-benzo[b]pyran (350 g) as an orange oil.

$^1$H-NMR (CDCl$_3$): δ=7.10(1H,dd), 6.96(1H,d), 6.59(1H, d), 5.96(1H,s), 1.78(3H,s), 1.35(6H,s) ppm.

PREPARATION 5

6-(4-Mehoxyphenyl)thio-2,2,3-trimethyl-2H-benzo[b]pyran

6-Bromo-2,2,3-trimethyl-2H-benzo[b]pyran (9.637 g) (see Preparation 4) was dissolved in absolute ethanol (200 ml), then sodium tert -butoxide (11.029 g), 4-methoxybenzenethiol (4.9 ml) and tetrakis (triphenylphosphine)palladium(0) (0.454 g) were added and the mixture was heated under reflux under a nitrogen atmosphere for 48 hours. The solvent was removed under reduced pressure and the residue was dissolved in dichloromethane and washed with water. The organic layer was dried (anhydrous sodium sulphate), the solvent was removed under reduced pressure and the crude product was chromatographed on silica using 1:1, hexane:dichloromethane as the eluent to yield 6-(4-methoxyphenyl)thio-2,2,3-trimethyl-2H-benzo[b]pyran (7.823 g) as a yellow oil.

$^1$H-NMR (CDCl$_3$): δ=7.28(2H,d), 7.05(1H,dd), 6.92(1H, d), 6.84(2H,d), 6.70(1H,d), 6.00(1H,s), 3.80(3H,s), 1.81(3H, s), 1.40(6H,s) ppm.

PREPARATION 6

6-(3-Methoxyphenyl)thio-2,2,3-trimethyl-2H-benzo[b]pyran

6-Bromo-2,2,3-trimethyl-2H-benzo[b]pyran (6.5 g) (see Preparation 4) was dissolved in absolute ethanol (135 ml), then sodium tert-butoxide (7.5 g), 3-methoxybenzenethiol (3.6 g) and tetrakis(triphenylphosphine)palladium(0) (0.35 g) were added and the mixture was heated under reflux under a nitrogen atmosphere for 48 hours. Further tetrakis (triphenylphosphine)palladium(0) (0.3 g) was added and heating was continued for a further 48 hours. The solvent was removed under reduced pressure and the residue was dissolved in dichloromethane and washed with water. The organic layer was dried (anhydrous sodium sulphate), the solvent removed under reduced pressure and the crude product chromatographed on silica using 1:1 hexane:dichloromethane as the eluent to yield 6-(3-methoxyphenyl)thio-2,2,3-trimethyl-2H-benzo[b]pyran (7.2 g) as an oil.

$^1$H-NMR (CDCl$_3$): δ=7.05–7.20(3H,m), 6.63–6.78(4H, m), 6.05(1H,s), 3.72(3H,s), 1.83(3H,s), 1.45(6H,s) ppm.

PREPARATION 7

6-(2-Methoxyphenyl)thio-2,2,3-trimethyl-2H-benzo[b]pyran

6-Bromo-2,2,3-trimethyl-2H-benzo[b]pyran (9.6 g) (see Preparation 4) was dissolved in absolute ethanol (200 ml), then sodium tert-butoxide (11.0 g), 2-methoxybenzenethiol (5.3 g) and tetrakis(triphenylphosphine)palladium(0) (0.45 g) were added and the mixture heated under reflux under a nitrogen atmosphere for 24 hours. The solvent was removed under reduced pressure and the residue was dissolved in dichloromethane and washed with water. The organic layer was dried (anhydrous sodium sulphate), the solvent was removed under reduced pressure and the crude product was chromatographed first on silica using 1:1 hexane:dichloromethane as the eluent and then on silica using 24:1 hexane:ethyl acetate as the eluent to yield 6-(2-methoxyphenyl)thio-2,2,3-trimethyl-2H-benzo[b]pyran (8.12 g) as an oil.

$^1$H-NMR (CDCl$_3$): δ=7.10–7.23(3H,m), 6.76–6.85(4H, m), 6.05(1H,s), 3.90(3H,s), 1.83(3H,s), 1.45(6H,s) ppm.

PREPARATION 8

6-(4-Hydroxyphenyl)thio-2,2,3-trimethyl-2H-benzo[b]pyran 6-(4-Methoxyphenyl)thio-2,2,3-trimethyl-2H-benzo[b] pyran (7.816 g) (see Preparation 5) was dissolved in dry 2,4,6-collidine (30 ml), anhydrous lithium iodide (10.04 g) was added and the mixture was heated under reflux under a nitrogen atmosphere for 48 hours. A further portion of lithium iodide (9.06 g). was then added and heating was continued for another 72 hours. After cooling, the mixture was taken up in dichloromethane and washed with 2N aqueous hydrochloric acid solution (×3). The organic layer was separated, dried (anhydrous sodium sulphate), the solvent removed under reduced pressure and the residue was chromatographed on silica using dichloromethane as the eluent to yield 6-(4-hydroxyphenyl)thio-2,2,3-trimethyl-2H-benzo[b]pyran (5.799 g) as an oil.

$^1$H-NMR (CDCl$_3$): δ=7.25(2H,d), 7.05(1H,dd), 6.92(1H, d), 6.70–6.80(3H,m), 6.02(1H,s), 4.92(1H,s), 1.85(3H,s), 1.40(6H,s) ppm.

PREPARATION 9

6-(3-Hydroxyphenyl)thio-2,2,3-trimethyl-2H-benzo[b]pyran 6-(3-Methoxyphenyl)thio-2,2,3-trimethyl-2H-benzo[b]pyran (3.5 g) (see Preparation 6) was dissolved in dry 2,4,6-collidine (15 ml), anhydrous lithium iodide (3 g) was added and the mixture was heated under reflux under a nitrogen atmosphere for 24 hours. After cooling, the mixture was taken up in dichloromethane and washed with 2N aqueous hydrochloric acid solution (×3). The-organic layer was dried (anhydrous sodium sulphate), the solvent removed under reduced pressure and the residue chromatographed on silica eluting with a solvent gradient of 1:1 hexane:dichloromethane changing to dichloromethane to yield 6-(3-hydroxyphenyl)thio-2,2,3-trimethyl-2H-benzo[b]pyran (2.25 g) as an oil.

$^1$H-NMR (CDCl$_3$): δ=7.05–7.21(3H,m), 6.75(2H,m), 6.60(2H,m), 6.04(1H,s), 4.60(1H,broad), 1.86(3H,s), 1.45 (6H,s) ppm.

PREPARATION 10

6-(2-Hydroxylhenyl)thio-2,2,3-trimethyl-2H-benzo[b]pyran 6-(2-Methoxyphenyl)thio-2,2,3-trimethyl-2H-benzo[b]pyran (3.5 g) (see Preparation 7) was dissolved in dry 2,4,6-collidine (15 ml), anhydrous lithium iodide (9.0 g) was added and the mixture was heated at 150° C for 40 hours. After cooling, the mixture was taken up in dichloromethane and washed with 2N aqueous hydrochloric acid solution (×3). The organic layer was dried (anhydrous sodium sulphate), the solvent removed under reduced pressure and the residue was chromatographed on silica using 1:1 hexane:dichloromethane as the eluent to yield 6-(2-hydroxyphenyl)thio-2,2,3-trimethyl-2H-benzo[b]pyran (1.2 g) as an oil.

$^1$H-NMR (CDCl$_3$): δ=7.50(1H,d), 7.31 (1H,t), 7.05(1H, d), 6.90(2H,m), 6.75(1H,d), 6.65(1H,d), 6.55(1lH,s), 5.99 (1H,s), 1.80(3H,s), 1.37(6H,s),

PREPARATION 11

6-(4-tert-Butyldimethylsilyloxyphenyl)thio-2,2,3-trimethyl-2H-benzo[b]pyran 6-(4-Hydroxyphenyl)thio-2,2,3-trimethyl-2H-benzo[b]pyran (5.799 g) (see Preparation 8) was dissolved in dry dimethylformamide (12 ml) and imidazole (2.768 g) and tert-butyidimethylsilyl chloride (2.923 g) were added. The flask was fitted with a calcium chloride drying tube and the mixture was stirred at 40° C. for 18 hours. The solvent was then removed under reduced pressure and the residue was partitioned between aqueous sodium bicarbonate solution and dichloromethane. The organic layer was dried (anhydrous sodium sulphate), the solvent removed under reduced pressure and the crude product chromatographed on silica using 1:1 hexane:dichloromethane as the eluent to yield 6-(4-tert-butyldimethylsilyloxyphenyl)thio-2,2,3-trimethyl-2H-benzo[b]pyran (6.681 g) as an oil. LRMS m/z=413 (m+1)$^+$.

$^1$H-NMR (CDCl$_3$): δ=7.20(2H,d), 7.05(i H,dd), 6.95(1H, d), 6.70–6.80(3H,m), 6.02(1H,s), 1.85(3H,s), 1.41 (6H,s), 0.97(9H,s), 0.21 (6H,s) ppm.

PREPARATION 12

6-(3-tert-butyldimethylsilyloxyphenyl)thio-2,2,3-trimethyl-2H-benzo[b]pyran 6-(3-Hydroxyphenyl)thio-2,2,3-trimethyl-2H-benzo[b]pyran (2.2 g) (see Preparation 9) was dissolved in dry dimethylformamide (4 ml) and imidazole (1.1 g) and tert-butyidimethylsilyl chloride (1.2 g) were added. The flask was fitted with a calcium chloride drying tube and the mixture was stirred at 40° C. for one hour. Water was added and the mixture was extracted with diethyl ether. The organic extract was washed with aqueous sodium hydrogen carbonate solution (×2), dried (anhydrous sodium sulphate), the solvent removed under reduced pressure and the crude product chromatographed on silica using (4:1 hexane:dichloromethane as the eluent to yield 6-(3-tert-Butyldimethylsilyloxyphenyl)thio-2,2,3-trimethyl-2H-benzo[b]pyran (2.84 g) as an oil.

$^1$H-NMR (CDCl$_3$): δ=7.00–7.18(3H,m), 6.74(2H,d), 6.58 (2H,m), 6.00(1H,s) 1.80(3H,s), 1.40(6H,s), 0.88(9H,s), 0.10 (6H,s) ppm.

PREPARATION 13

6-(2-tert-Butyldimethylsilyloxyphenyl)thio-2,2,3-trimethyl-2H-benzo[b]pyran 6-(2-hydroxyphenyl)thio-2,2,3-trimethyl-2H-benzo[b]pyran (1.1 g) (see Preparation 10) was dissolved in dry dimethylformamide (2 ml) and imidazole (0.55 g) and tert-butyidimethylsilyl chloride (0.61 g) were added. The flask was fitted with a calcium chloride drying tube and the mixture stirred at 40° C for 90 minutes. Water was added and the mixture was extracted with diethyl ether. The organic extract was washed with aqueous sodium hydrogen carbonate solution (×2), dried (anhydrous sodium sulphate), the solvent removed under reduced pressure and the crude product was chromatographed on silica using 4:1 hexane:dichloromethane as the eluent to yield 6-(2-tert-butyldimethylsilyloxyphenyl)thio-2,2,3-trimethyl-2H-benzo[b]pyran (1.43 g) as an oil.

$^1$H-NMR (CDCl$_3$): δ=7.20(1H,dd), 7.00(2H,m), 6.78(4H, m), 6.05(1H,s), 1.83(3H,s), 1.45(6H,s), 1.05(9H,s), 0.28 (6H,s) ppm.

PREPARATION 14

(3S,4S)-6-(4-tert-Butyldimethylsilyloxyphenyl) sulphonyl-3,4-dihydro-3,4-epoxy-2,2,3-trimethyl-2H-benzo[b]pyran 6-(4-tert-butyldimethylsilyloxyphenyl)thio-2,2,3-trimethyl-2H-benzo[b]pyran (2.182 g) (see Preparation 11) and [(S,S)-1,2-bis(3,5-di-tert-Butylsalicylideamino)]

cyclohexane manganese(III) chloride (see J.Am.Chem.Soc., 1991, 113, 7063) (0.25 g) were dissolved in dichloromethane (10 ml) and 3M aqueous sodium hypochlorite solution (50 ml, prepared from 4M commercial bleach) was added. The two phase system was stirred vigorously for 20 hours and then diluted with dichloromethane (30 ml) before separation of the two layers. The organic layer was dried (anhydrous sodium sulphate), the solvent removed under reduced pressure and the residue was chromatographed on silica using dichloromethane as the eluent to give (3S,4S)-6-(4-tert-butyldimethylsilyloxyphenyl)sulphonyl-3,4-dihydro-3,4-epoxy-2,2,3-trimethyl-2H-benzo[b]pyran (1.907 g). HPLC confirmed that this product consisted of a single enantiomer. LRMS m/z=478 (M+NH$_4$)$^+$.

$^1$H-NMR (CDCl$_3$): δ=7.90(1H,d), 7.75(3H,m), 6.90(3H, m), 3.70(1H,d), 1.56(3H,s), 1.51(3H,s), 1.26(3H,s), 0.98 (9H,s), 0.25(6H,s) ppm.

PREPARATION 15

(3S,4S)-6-(3-tert-Butyldimethylsilyloxyphenyl) sulphonyl-3,4-dihydro-3,4-epoxy-2,2,3-trimethyl-2H-benzo[b]pyran 6-(3-tert-Butyldimethylsilyloxyphenyl)thio-2,2,3-trimethyl-2H-benzo[b]pyran (21.0 g) (see Preparation 12), 4-phenylpyridine-N-oxide (2.2 g) and [(S,S)-1,2-bis(3,5-di-tert-butylsalicylideamino)]cyclohexane manganese (III) chloride (see J.Am.Chem.Soc., 1991, 113, 7063) (2.25 g) were dissolved in dichloromethane (120 ml) and 3M aqueous sodium hypochlorite solution (500 ml, prepared from 4M commercial bleach) was added. The two phase system was stirred vigorously for 24 hours, diluted with dichloromethane and filtered through a cellulose-based filter aid before separation of the two layers. The organic layer was then washed with brine, dried (anhydrous sodium sulphate), the solvent removed under reduced pressure and the residue chromatographed on silica using dichloromethane as the eluent to give (3S,4S)-6-(3-tert-butyldimethylsilyloxyphenyl)sulphonyl-3,4-dihydro-3,4-epoxy-2,2,3-trimethyl-2H-benzo[b]pyran (23.6 g). HPLC confirmed that this product consisted of a single enantiomer. LRMS m/z=461 (m+1)$^+$.

$^1$H-NMR (CDCl$_3$): δ=7.90(1H,d), 7.78(1H,dd), 7.45(1H, d), 7.35(2H,m), 7.00(1H,dd), 6.88(1H,d), 3.70(1H,s), 1.55 (3H,s), 1.50(3H,s), 1.30(3H,s), 0.97(9H,s), 0.21(6H,s) ppm.

PREPARATION 16

(3S,4S)-6-(2-tert-Butyldimethylsilyloxyphenyl) sulphonyl-3,4-dihydro-3,4-epoxy-2,2,3-trimethyl-2H-benzo[b]pyran 6-(2-tert-butyldimethylsilyloxyphenyl)thio-2,2,3-trimethyl-2H-benzo[b]pyran (1.4 g) (see Preparation 13) and [(S,S)-1,2-bis(3,5-di-tert-butylsalicylideamino)] cyclohexane manganese(III) chloride (see J.Am.Chem.Soc., 1991, 113, 7063) (0.15 g) were dissolved in dichloromethane (7 ml) and 3M aqueous sodium hypochlorite solution (32 ml, prepared from 4M commercial bleach) was added. The two phase system was stirred vigorously for 24 hours and then diluted with dichloromethane before separation of the two layers. The organic layer was dried (anhydrous sodium sulphate), the solvent removed under reduced pressure and the residue chromatographed on silica using dichloromethane as the eluent to give (3S,4S)-6-(2-tert-butyldimethylsilyloxyphenyl)sulphonyl-3,4-dihydro-3,4-epoxy-2,2,3-trimethyl-2H-benzo[b]pyran (1.2 g). LRMS m/z=461 (m+1)$^+$.

$^1$H-NMR (CDCl$_3$): δ=8.10(1H,dd), 7.85(1H,d), 7.72(1H, dd), 7.45(1H,t), 7.10(1H,t), 6.82(2H,m), 3.68(1H,s), 1.57 (3H,s), 1.50(3H,s), 1.28(3H,s), 0.95(9H,s), 0.30(6H,s) ppm.

PREPARATION 17

(3S,4S)-3,4-Dihydro-3,4-epoxy-6-(3-methoxyphenyl)sulphonyl-2,2,3-trimethyl-2H-benzo[b]pyran 6-(3-Methoxyphenyl)thio-2,2,3-trimethyl-2H-benzo[b] pyran (4.2 g) (see Preparation 6) and [(S,S)-1,2-bis(3,5-di-tert-butylsalicylideamino)]-cyclohexane manganese(III) chloride (see J.Am. Chem.Soc., 1991, 113, 7063) (0.60 g) were dissolved in dichloromethane (30 ml) and 3M aqueous sodium hypochlorite solution (130 ml, prepared from 4M commercial bleach) was added. The two phase system was stirred vigorously for 24 hours and then diluted with dichloromethane. The mixture was filtered through a cellulose-based filter aid before separation of the two layers. The organic layer was dried (anhydrous sodium sulphate), the solvent removed under reduced pressure and the residue chromatographed on silica using dichloromethane as the eluent to give (3S,4S)-3,4-dihydro-3,4-epoxy-6-(3-methoxyphenyl)sulphonyl-2,2,3-trimethyl-2H-benzo[b] pyran (2.0 g) as a light yellow foam. LRMS m/z=361 (m+1)$^+$.

$^1$H-NMR (CDCl$_3$): δ=7.90(1H,d), 7.78(1H,dd), 7.40–7.50(3H,m), 7.08(1H,dd), 6.89(1H,d), 3.85(3H,s), 3.72(1H,s), 1.55(3H,s), 1.50(3H,s), 1.27(3H,s) ppm.

PREPARATION 18

(3S,4R)-4-Amino-3,4-dihydro-3-hydroxy-6-(3-methoxyphenyl)sulphonyl-2,2,3-trimethyl-2H-benzo[b]pyran (3S,4S)-3,4-Dihydro-3,4-epoxy-6-(3-methoxyphenyl) sulphonyl-2,2,3-trimethyl-2H-benzo[b]pyran (2.0 g) (see Preparation 17) was dissolved in ethanol (15 ml) and 35% aqueous ammonia solution (10 ml) was added. The mixture was heated at 50° C. for 48 hours before adding further ammonia solution (5 ml) and heating for another 8 hours. The solvent was removed under reduced pressure and the residue was chromatographed on silica using 5:95 methanol:dichloromethane as the eluent to yield (3S,4R)-4-amino-3,4-dihydro-3-hydroxy-6-(3-methoxyphenyl)sulphonyl-2,2, 3-trimethyl-2H-benzo[b]pyran (1.9 g) as a foam. Found: C,58.65; H,5.77; N,3.29. C$_{19}$H$_{23}$NO$_5$S, 0.22 CH$_2$Cl$_2$ requires C,58.28; H,5.96; N,3.53%.

$^1$H-NMR (CDCl$_3$): δ=8.00(1H,s), 7.70(1H,dd), 7.38–7.52 (3H,m), 7.08(1H,dd), 6.85(1H,d), 3.90(1H,s), 3.85(3H,s), 2.60(1H,broad), 1.55(2H,broad), 1.49(3H,s), 1.30(3H,s), 1.01(3H,s) ppm.

PREPARATION 19

(3S,4R)-4-(2-Chloropyrimidin-4-yl)amino-3,4-dihydro-3-hydrox-6-(3-methoxyphenyl)sulphonyl-2,2,3-trimethyl-2H-benzo[b]pyran and (3S,4R)-4-(4-chloropyrimidin-2-yl) amino-3,4-dihydro-3-hydroxy-6-(3-methoxyphenyl) sulphonyl-2,2,3-trimethyl-2H-benzo[b]pyran (3S,4R)-4-Amino-3,4-dihydro-3-hydroxy-6-(3-methoxyphenyl)-sulphonyl-2,2,3-trimethyl-2H-benzo[b] pyran (0.95 g) (see Preparation 18) was dissolved in dry 1,4-dioxane (10 ml), 2,4-dichloropyrimidine (0.45 g) and diisopropylethylamine (0.39 g) were added and the mixture was heated under reflux for 25 hours. The solvent was removed under reduced pressure and the residue was azeotroped with dichloromethane then chromatographed on silica using 4:1 dichloromethane:ethyl acetate as the eluent to first yield (3S,4R)-4-(4-chloropyrimidin-2-yl)amino-3,4-dihydro-3-hydroxy-6-(3-methoxyphenyl)-sulphonyl-2,2,3-trimethyl-2H-benzo[b]pyran (0.25 g) as a foam. LRMS m/z=490(m)$^+$.

1H-NMR (CDCl$_3$): $\delta$=8.01 (1H,d), 7.80(1H,dd), 7.38–7.50(4H,m), 7.05(1H,dd), 6.90(1H,dd), 6.80(1H, broad), 5.75(1H,broad), 5.47(1H,d), 4.95(1H,broad), 3.80 (1H,s), 1.50(3H,s), 1.45(3H,s), 1.13(3H,s) ppm.

Further elution with 1:1 dichloromethane:ethyl acetate provided (3S,4R)-4-(2-chloropyrimidin-4-yl)amino-3,4-dihydro-3-hydroxy-6-(3-methoxyphenyl)sulphonyl-2,2,3-trimethyl-2H-benzo[b]pyran (0.64 g) as a white solid, m.p. 228–230° C. LRMS m/z=490(m)$^+$.

$^1$H-NMR (CDCl$_3$): $\delta$=8.07(1H,d), 7.85(1H,s), 7.70(1H, dd), 7.35–7.45(3H,m), 7.08(1H,dd), 6.90(1H,dd), 6.61(1H, dd), 5.79(1H,d), 5.50(1H,broad), 4.65(1H,broad), 3.85(3H, s), 1.50(3H,s), 1.40(3H,s), 1.15(3H,s) ppm.

PREPARATION 20

(3S,4R)-4-Amino-3,4-dihydro-3-hydroxy-6-(3-hydroxyphenyl)sulphonyl-2,2,3-trimethyl-2H-benzo[b]pyran (3S,4S)-6-(3-tert-butyldimethylsilyloxyphenyl) sulphonyl-3,4-dihydro-3,4-epoxy-2,2,3-trimethyl-2H-benzo [b]pyran (2.2 g) (see Preparation 15) was dissolved in ethanol (25 ml) and 35% aqueous ammonia solution (25 ml) was added. The mixture was heated at 40–50° C. for 24 hours. The solvent was removed under reduced pressure and the residue was chromatographed on silica using 7.5:92.5 methanol:dichloromethane as the eluent to yield (3S,4R)-4-amino-3,4-dihydro-3-hydroxy-6-(3-hydroxyphenyl) sulphonyl-2,2,3-trimethyl-2H-benzo[b]pyran (1.42 g) as a foam. Found: C,54.39; H,5.22; N,3.19. C$_{18}$H$_{21}$NO$_5$S, 0.50 CH$_2$Cl$_2$ requires C,54.75; H,5.46; N,3.45%.

$^1$H-NMR (CDCl$_3$): $\delta$=8.07(1H,s), 7.70(1H,dd), 7.50(1H, s), 7.41 (1H,d), 7.30(1H,d), 6.99(1H,dd), 6.81(1H,d), 3.99 (1H,s), 3.50(2H,broad), 1.48(3H,s), 1.28(3H,s), 1.00(3H,s) ppm.

PREPARATION 21

1,2-Dihydro-4-hydroxy-2-methyl-1-oxophthalazin

Phthalic anhydride (7.4 g) was dissolved in hot acetic acid (50 ml) and a solution of methylhydrazine (2.7 ml) in water (50 ml) was added. The mixture was heated under reflux for 15 minutes and left to cool overnight. The precipitate that formed was filtered off, washed with water and dried under reduced pressure at 65° C. to yield 1,2-dihydro-4-hydroxy-2-methyl-1-oxophthalazin (7.6 g) as a white solid. m.p. 243–244° C.

$^1$H-NMR (CD$_3$OD): $\delta$=8.28(1H,m), 8.05(1H,m), 7.85 (2H,m), 4.87(1H,s), 3.66(3H,s) ppm.

PREPARATION 22

1,2-Dihydro-4-hydroxy-1-methyl-2-oxopyridine 2,4-Dihydroxypyridazine (3.0 g) was dissolved in 2N aqueous sodium hydroxide solution (30 ml) and dimethyl sulphate (3.7 g) was added dropwise over 90 minutes. The mixture was stirred at room temperature overnight, acidified with concentrated hydrochloric acid, the solvent removed under reduced pressure, the residue stirred in 5% methanol/dichloromethane and filtered. The filtrate was evaporated and the crude product was chromatographed on silica using 7:93 methanol:dichloromethane as the eluent to yield 1,2-dihydro-4-hydroxy-1-methyl-2-oxopyridine (0.77 g) as a yellow solid. m.p. 165–169° C. Found: C,57.28; H,5.47; N,10.89. C$_6$H$_7$NO$_2$ requires C,57.59; H,5.64; N,11.19%.

$^1$H-NMR (d$_6$-DMSO): $\delta$=10.50(1H,d), 7.50(1H,d), 5.82 (1H,dd), 5.55(1H,d), 3.30(3H,s) ppm.

PREPARATION 23

2,4-Dihydroxy-5,6-dimethylpyridine 5,6-Dimethyl-4-hydroxy-2-oxo-2H-pyran (11.92 g) (see J.C.P.Perkin Trans. 1, 1980, 2272) was dissolved in 1,4-dioxane (80 ml), aqueous 35% ammonia solution (40 ml) was added and the mixture was heated under reflux for 90 minutes. The solution was left to cool overnight, the precipitate filtered off and dried under reduced pressure at 90° C. for 24 hours to yield 2,4-dihydroxy-5,6-dimethylpyridine (3.47 g) as a white solid.

$^1$H-NMR (d$_6$-DMSO): $\delta$=10.75(1H,broad), 5.42(l1H,s), 2.09(3H,s), 1.78(3H,s) ppm.

PREPARATION 24

6-(3,4-Dimethgxyphenyl)thio-2,2,3-trimethyl-2H-benzo[b]pyran

6-Bromo-2,2,3-trimethyl-2H-benzo[b]pyran (7.4 g) (see Preparation 4) was dissolved in absolute ethanol (15 ml), sodium tert-butoxide (8.5 g), 3,4-dimethoxybenzenethiol (5 g) and tetrakis(triphenylphosphine)palladium(0) (0.5 g) were added and the mixture was heated under reflux under a nitrogen atmosphere for 24 hours. A further portion of tetrakis(triphenylphosphine)palladium(0) (0.5 g) was then added and heating was continue d for another 24 hours. The sol vent was remove d under reduced pressure and the residue was taken up in dichloromethane and washed with water. The organic layer was dried (anhydrous sodium sulphate), the solvent removed under reduced pressure and the crude product chromatographed on silica using 1:4 hexane:dichloromethane as the eluent to yield. 6-(3,4-dimethoxyphenyl)thio-2,2,3-trimethyl-2H-benzo[b]pyran (7.4 g) as a yellow oil.

$^1$H-NMR (CDCl$_3$): $\delta$=7.20(1H,dd), 6.85–7.00(3H,m), 6.80(3H,d), 6.72(1H,d), 6.03(1H,s), 3.85(3H,s), 3.80(3H,s), 1.85(3H,s), 1.41(6H,s) ppm.

PREPARATION 25

(3S,4S)-3,4-Dihydro-6-(3,4-dimethoxyphenyl) sulphonyl-3,4-epoxy-2,2,3-trimethyl-2H-benzo[b] pyran 6-(3,4-Dimethoxyphenyl)thio-2,2,3-trimethyl-2H-benzo [b]pyran (3.1 g) (see Preparation 24), 4-phenylpyridine-N-oxide (0.4 g) and [(S,S)-1,2-bis(3,5-di-tert-butylsalicylideamino)]cyclohexane manganese(III) chloride (see J.Am.Chem.Soc., 1991, 113, 7063) (0.4 g) were dissolved in dichloromethane (35 ml) and 3M aqueous sodium hypochlorite solution (100 ml, prepared from 4M commercial bleach) was added. The two phase system was stirred vigorously for 24 hours and then diluted with dichloromethane before separation of the two layers. The organic layer was dried (anhydrous sodium sulphate), the solvent removed under reduced pressure and the residue was chromatographed on silica using 19:1 dichloromethane:ethyl acetate as the eluent to give (3S,4S)-3,4-dihydro-6-(3,4- dimethoxyphenyl)sulphonyl-3,4-epoxy-2,2,3-trimethyl-2H-benzo[b]pyran (3.0 g) as a yellow foam. LRMS m/z=408 (m +NH$_4$)$^+$.

$^1$H-NMR (CDCl$_3$): δ=7.89(1H,d), 7.75(1H,dd), 7.53(1H, dd), 7.35(1H,d), 6.80–7.00(2H,m), 3.92(6H,s), 3.71(1H,s), 1.59(3H,s), 1.52(3H,s), 1.29(3H,s) ppm.

PREPARATION 26

(3S,4R)-3,4-Dihydro-4-(2,3-dihydro-2-methyl-3-oxopyridazin-6-yl)oxy-6-(3,4-dimethoxyphenyl) sulphonyl-3-hydroxy-2,2,3-trimethyl-2H-benzo[b] pyran (3S,4S)-3,4-Dihydro-6-(3,4-dimethoxyphenyl)sulphonyl-3,4-epoxy-2,2,3-trimethyl-2H-benzo[b]pyran (3.0 g) (see Preparation 25) and 2,3-dihydro-2-methyl-3-oxo-6-hydroxypyridazin (2.0 g) (see J.Org.Chem, 1971, 36, 3372) were suspended in dry 1,4-dioxane (30 ml), pyridine (0.61 g) was added and the mixture heated under reflux (a calcium chloride drying tube was attached to the flask) for 2 days. The solvent was removed under reduced pressure, the residue stirred with 5% methanol/dichloromethane and filtered. The filtrate was evaporated and the crude product chromatographed on silica eluting with 2.5:97.5 methanol:dichloromethane as the eluent to yield (3S,4R)-3,4-dihydro-4-(2, 3-dihydro-2-methyl-3-oxo-pyridazinyl-6-yl)oxy-6-(3,4-dimethoxyphenyl)sulphonyl-3-hydroxy-2,2,3-trimethyl-2H-benzo[b]pyran (1.7 g) as a yellow foam.

$^1$H-NMR (CDCl$_3$): δ=7.90(1H,d), 7.75(1H,dd), 7.52(1H, dd), 7.35(1H,s), 7.10(2H,m), 6.90(2H,m), 5.90(1H,s), 3.92 (3H,s), 3.90(3H,s), 3.70(3H,s), 1.50(3H,s), 1.40(3H,s), 1.25 (3H,s) ppm.

PREPARATION 27

6-Bromo-3,4-dihydro-4-oxo-2,2,3-trimethyl-2H-benzo[b]pyran (Alternative route to the compound of Preparation 3)

a) 1-(5-Bromo-2-hydroxyphenyl)propane-1-one

To a stirred mixture of aluminium trichloride (2.5 kg) in dichloromethane (5000 ml) at room temperature was added propanoyl chloride (864 g) over a 5 minute period. The mixture was stirred for 45 minutes at room temperature and then a solution of 4-bromoanisole (875 g) in dichloromethane (1000 ml) was added over 15 minutes. The reaction was heated under reflux for 6 hours then cooled and stirred at room temperature overnight.

The reaction was quenched by pouring slowly onto ice (11 kg) over a 40 minute period. The mixture was stirred for 30 minutes and the layers separated. The aqueous layer was further extracted with dichloromethane (2×1000 ml) and the combined organic extracts washed with water (2×2000 ml). Two-thirds of the solvent was removed from the organic layer by distillation at atmospheric pressure. Methanol (3750 ml) was slowly added whilst continuing with the distillation. The distillation was continued until a pot temperature of 64° C. and a head temperature of 62° C. was achieved. Water (270 ml) was then added to the solution at this temperature and the reaction cooled to precipitate an off-white solid. When the reaction mixture had cooled to 20° C., further water (270 ml) was slowly added and the mixture granulated at about 10° C. for 2 hours.

The solid was filtered off and sparingly washed on the pad with methanol:water (6:1, by volume), then dried under reduced pressure at 50° C. to yield the title compound (960 g).

b) 6-Bromo-3,4-dihydro4-oxo-2,2,3-trimethyl-2H-benzo[b] pyran.

To a stirred solution of the product of part (a) (1.46 kg) in acetone (7300 ml) and xylene (6570 ml) was added piperidine (3.04 kg) and the reaction heated under reflux for 5 days.

The reaction was cooled and washed successively with water (2×3000 ml) followed by 2N aqueous hydrochloric acid, solution (2×5000 ml) (with ice-cooling), 2N aqueous sodium hydroxide solution (3000 ml) and water (2×3000 ml).

The organic layer was concentrated under reduced pressure to provide the title compound as a brown oil (1.46 kg).

Pharmacological Data

A representative selection of the compounds of the preceding Examples was tested for smooth muscle relaxant activity by the method involving measuring the in vitro relaxation of electrically stimulated guinea pig tracheal ring preparations as described on pages 18 and 19 of the description.

The results are shown in the Table below in which the minimum dose[1] of compound which causes maximal inhibition of the cholinergic contraction relative to control was determined.

TABLE

| Example no. | Minimum dose[1] (μM) |
| --- | --- |
| 1 | 0.1 |
| 2 | 0.3 |
| 3 | 0.1 |
| 4 | 0.03 |
| 5 | 0.01 |
| 9 | 0.3 |
| 12 | 0.1 |

We claim:

1. A compound of the formula:

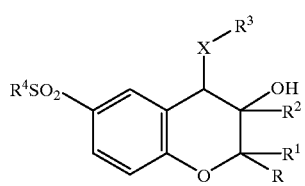

(I)

or a pharmaceutically acceptable salt thereof, wherein X is O, S or NH;

R and R$^1$ are each independently selected from H and C$_1$–C$_4$ alkyl or taken together represent C$_2$–C$_6$ alkylene;

R$^2$ is H or C$_1$–C$_4$ alkyl;

R$^3$ is (a) a 6-membered heterocyclic ring containing 1 N-hetero atom, said ring being linked to X by a ring carbon atom, optionally benzo-fused and optionally substituted, including in the benzo-fused portion, C$_1$–C$_6$ alkyl, hydroxy, —OR$^5$, halo, —S(O)$_m$R$^5$, oxo, amino, —NHR$^5$, —N(R$^5$)$_2$, cyano, —CO$_2$R$^5$, —CONH$_2$, —CONHR$^5$ or —CON(R$^5$)$_2$, with the proviso that R$^3$ is not an N-(C$_1$–C$_6$ alkyl)pyridonyl group;

(b), when X is NH, a group of the formula:

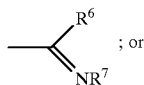 ; or (c), when X is NH, a group of the formula:

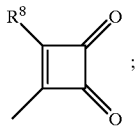 ;

R⁴ is phenyl substituted by a hydroxy group and optionally further substituted by 1 or 2 substitutents each independently selected from hydroxy, $C_1$–$C_6$ alkyl, —OR⁵, halo, cyano and nitro;

R⁵ is $C_1$–$C_6$ alkyl;

R⁶ is —OR⁵, —NHR⁵, —N(R⁵)₂, —SR⁵ or —NHR⁹;

R⁷ is cyano;

R⁸ is —OR⁵, —NHR⁵, —N(R⁵)₂, or —NHR⁹;

R⁹ is phenyl optionally substituted by $C_1$–$C_6$ alkyl, hydroxy, —OR⁵, halo, cyano or nitro; and m is 0, 1 or 2.

2. A compound as claimed in claim 1 wherein

X is O or NH;

R, R¹ and R² are each $C_1$–$C_4$ alkyl;

R³ is (a) a 6-membered heterocyclic ring containing 1 N hetero-atom, said ring being optionally benzo-fused and optionally substituted, including in the benzo-fused portion, by $C_1$–$C_4$ alkyl, hydroxy, halo or oxo, (b) is a group of the formula:

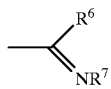

or (c) is a group of the formula:

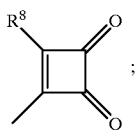 ;

R⁴ is phenyl substituted by 1 or 2 hydroxy groups;

R⁶ is —SR⁵; R⁸ is —OR⁵; and R⁵ and R⁷ are as defined in claim 1.

3. A compound as claimed in claim 2 wherein

X is O;

R, R¹ and R² are each methyl;

R³ is 1,2-dihydro-2-oxo-1H-pyridin-4-yl, 1,2-dihydro-5,6-dimethyl-2-oxo-1H-pyridin-4-yl, 3,4-dioxo-2-ethoxycyclobut-1-en-1-yl or -cyano-2-methylisothioureido;

and R⁴ is 2-hydroxyphenyl, 3-hydroxyphenyl, 4-hydroxyphenyl or 3,4-dihydroxyphenyl.

4. A compound as claimed in claim 3 wherein R³ is 1,2-dihydro-2-oxo-1H-pyridin-4-yl; and R⁴ is 3-hydroxyphenyl or 4-hydroxyphenyl.

5. A compound as claimed in claim 1 of the formula:

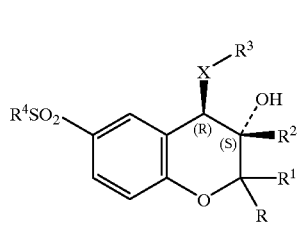

(IA)

where X, R, R¹, R², R³ and R⁴ are as defined in claim 1.

6. A pharmaceutical composition comprising a compound of the formula (I), or a pharmaceutically acceptable salt thereof, as claimed in claim 1, together with a pharmaceutically acceptable diluent or carrier.

7. A method of treating a disease associated with the altered tone and/or motility of smooth muscle, comprising administering to a person in need of such treatment an effective amount of a compound of formula (I) as defined in claim 1, or a pharmaceutically acceptable salt or composition thereof.

8. A method as claimed in claim 7 where the disease is chronic obstructive airways disease, asthma, urinary incontinence, irritable bowel syndrome, diverticular disease, oesophageal achalasia or hypertension.

9. A compound of the formula:

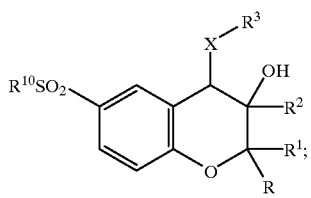

(II)

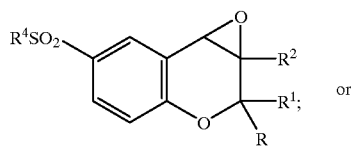 or (III)

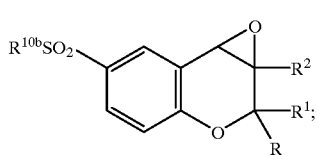 ;

(VIA)

wherein

X is O, S or NH;

R and R¹ are each independently selected from H and $C_1$–$C_4$alkyl or taken together represent $C_2$–$C_6$ alkylene;

R² is H or $C_1$–$C_4$ alkyl;

R³ is (a) a 6-membered heterocyclic ring containing 1 N-hetero atom, said ring being linked to X by a ring carbon atom, optionally benzo-fused and optionally substituted, including in the benzo-fused portion, $C_1$–$C_6$ alkyl, hydroxy, —OR⁵, halo, —S(O)$_m$R⁵, oxo, amino, —NHR⁵, —N(R⁵)₂, cyano, —CO₂R⁵, —CONH₂, —CONHR⁵ or —CON(R⁵)₂, with the proviso that R³ is not an N-($C_1$–$C_6$ alkyl)pyridonyl group;

(b), when X is NH, a group of the formula:

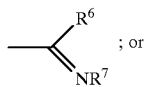

; or (c), when X is NH, a group of the formula:

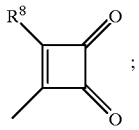

;

$R^5$ is $C_1$–$C_6$ alkyl;
$R^5$ is —$OR^5$, —$NHR^5$, —$N(R^5)_2$, —$SR^5$ or —$NHR^9$;
$R^7$ is cyano;
$R^8$ is —$OR^5$, —$NHR^5$, —$N(R^5)_2$, or —$NHR^9$;
$R^9$ is phenyl optionally substituted by $C_1$–$C_6$ alkyl, hydroxy, —$OR^5$, halo, cyano or nitro;

$R^{10}$ is phenyl substituted by a protected hydroxy group and optionally further substituted by 1 or 2 substituents each independently selected from a protected hydroxy group, hydroxy, $C_1$–$C_6$ alkyl, —$OR^5$, halo, cyano and nitro;

$R^{10b}$ is phenyl substituted by a tri($C_1$–$C_4$ alkyl)silyloxy group and optionally further substituted by 1 or 2 substituents each independently selected form tri($C_1$–$C_4$ alkyl)silyloxy, hydroxy, $C_1$–$C_6$ alkyl, —$OR^5$, halo, cyano and nitro; and X, R, $R^1$, $R^2$, $R^3$, and $R^5$ are as defined in claim 1; and m is 0, 1 or 2.

10. A compound of the formula (VIA) as claimed in claim 9 wherein the tri($C_1$–$C_4$ alkyl)silyloxy group in the definition of $R^{10b}$ is tert-butyldimethylsilyloxy, or a compound of the formula (II) as claimed in claim 9 wherein the protected hydroxy group in the definition of $R^{10}$ is $C_1$–$C_4$ alkoxy or tri($C_1$–$C_4$ alkyl)silyloxy.

11. A compound of the formula (II) as claimed in claim 10 wherein the protected hydroxy group in the definition of $R^{10}$ is methoxy or tert-butyldimethylsilyloxy.

* * * * *